(12) United States Patent
Orazov et al.

(10) Patent No.: US 9,809,528 B2
(45) Date of Patent: Nov. 7, 2017

(54) PRODUCTION OF ALPHA-HYDROXY CARBOXYLIC ACIDS AND ESTERS FROM HIGHER SUGARS USING TANDEM CATALYST SYSTEMS

(71) Applicant: CALIFORNIA INSTITUTE OF TECHNOLOGY, Pasadena, CA (US)

(72) Inventors: Marat Orazov, Pasadena, CA (US); Mark E. Davis, Pasadena, CA (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 15/207,822

(22) Filed: Jul. 12, 2016

(65) Prior Publication Data

US 2017/0015614 A1 Jan. 19, 2017

(51) Int. Cl.
*C07C 67/00* (2006.01)
*C07C 51/00* (2006.01)

(52) U.S. Cl.
CPC .............. *C07C 67/00* (2013.01); *C07C 51/00* (2013.01)

(58) Field of Classification Search
CPC ................................ C07C 51/00; C07C 67/00
See application file for complete search history.

(56) References Cited

U.S. PATENT DOCUMENTS

| | | | | |
|---|---|---|---|---|
| 4,792,620 A | * | 12/1988 | Paulik | B01J 31/0231 560/232 |
| 2010/0121096 A1 | * | 5/2010 | Taarning | C07C 51/00 560/179 |

OTHER PUBLICATIONS

Holm et al, Science, Conversion of Sugars to Lactic Acid Derivatives Using Heterogeneous Zeotype Catalysts, Apr. 30, 2010, 328, pp. 602-606.*
Gibson, Biomass Magazine, Converting Carbs to Lactic Acid with Catalysts, 2010, p. 1, recovered from http://biomassmagazine.com/articles /3778/converting-carbs-to-lactic-acid-with-catalysts on Dec. 5, 2016.*
Bermejo-Deval et al., "Active Sites in Sn-Beta for Glucose Isomerization to Fructose and Epimerization to Mannose", ACS Catal., 2014, 4 (7), 2288-2297.
Bilik et al., "Reactions of saccharides catalyzed by molybdate ions. XV.* Mechanism of the epimerization reaction", Chem Zvesti, 1975, 29 (5), 690-696.
Caldeira et al., "Complexes of Mo(VI) with Lactic, Thiolactic and Thiomalic Acids Studied by NMR Spectroscopy", Polyhedron, 1986, 5 (1-2), 381-385.
Dapsens et al., "A continuous process for glyoxal valorization using tailored Lewis-acid zeolite catalysts", Green Chem, 2014, 16 (3), 1176-1186.
Dusselier et al., "Mechanistic Insight into the Conversion of Tetrose Sugars to Novel a-Hydroxy Acid Platform Molecules", Chem Cat Chem, 2013, 5 (2), 569-575.
Dusselier et al., "Lactic acid as a platform chemical in the biobased economy: the role of chemocatalysis", Energy Environ. Sci., 2013, 6 (5), 1415-1442.
Gibson, "Converting carbs to lactic acid with catalysts", Biomassmagazine.com, May 2010, http://biomassmagazine.com/articles/3778/converting-carbs-to-lactic-acid-with-catalysts, 1 page.
Hayes et al., "Epimerization of Aldoses by Molybdate Involving a Novel Rearrangement of the Carbon Skeleton", J. Am. Chem. Soc., 1982, 104 (24), 6764-6769.
Holm et al., "Conversion of Sugars to Lactic Acid Derivatives Using Heterogeneous Zeotype Catalysts", Science, 2010, 328 (5978), 602-605.
Hricoviniováet al., "Structure of 2-C-(hydroxymethyl)-D-ribose (hamamelose) in the solid-state analyzed by CP MAS NMR and X-ray crystallography", Carbohydr Res., 2005, 340 (3), 455-458.
Hricoviniováet al., "Stereospecific Molybdic Acid-Catalyzed Isomerization of D-Fructose ato Branched-Chain Aldose. The Synthesis of D-Hamamelose", Chem. Pap., 1998, 52 (5), 692-698.
Huber et al., "Synthesis of Transportation Fuels from Biomass: Chemistry, Catalysts, and Engineering", Chem. Rev., 2006, 106 (9), 4044-4098.
Matulova et al., "Reactions of saccharides catalyzed by molybdate ions XLI.* NMR spectra of 2-ketoses in molybdate complexes", 1990, 44 (1), 97-103.
Osmundsen et al., "Tin-containing silicates: structure-activity relations", Proc. Royal. Soc. A, 2012, 468 (2143), 2000-2016.
Petrušet al., "The Bilik Reaction", Topics in Current Chemistry, 2001, 15-41.
Rasrendra et al., "Catalytic Conversion of Dihydroxyacetone to Lactic Acid Using Metal Salts in Water", ChemSusChem, 2011, 4, 768-777.
Sauvage et al., "A multinuclear NMR spectroscopy study of the tungstate and molybdate complexes of D-fructose and L-sorbose", Carbohydr. Res., 1996, 286 (6), 67-76.
Stankovićet al., "Reactions of saccharides catalyzed by molybdate ions. XIV.* Epimerization of pentuloses", Chem Zvesti, 1975, 29 (5), 685-689.
Taarning et al., "Zeolite-Catalyzed Isomerization of Triose Sugars", ChemSusChem, 2009, 2 (7), 625-627.
Tanase et al., "Novel C-2 Epimerization of Aldoses Promoted by Nickel(II) Diamine Complexes, Involving a Stereospecific Pinacol-Type 1,2-Carbon Shift", Inorg. Chem., 1988, 27 (23), 4085-4094.
Tolborg et al., "Tin-containing Silicates: Alkali Salts Improve Methyl Lactate Yield from Sugars", ChemSusChem, 2015, 8 (4), 613-617.

(Continued)

*Primary Examiner* — Paul A Zucker
(74) *Attorney, Agent, or Firm* — Baker & Hostetler LLP

(57) ABSTRACT

The present disclosure is directed to methods and composition used in the preparation of alpha-hydroxy carboxylic acids and esters from higher sugars using a tandem catalyst system comprising retro-aldol catalysts and Lewis acid catalysts. In some embodiments, these alpha-hydroxy carboxylic acids may be prepared from pentoses and hexoses. The retro-aldol and Lewis catalysts may be characterized by their respective ability to catalyze a 1,2-carbon shift reaction and a 1,2-hydride shift reaction on an aldose or ketose substrate.

15 Claims, 13 Drawing Sheets

(56) References Cited

OTHER PUBLICATIONS

Wang et al., "Chemical synthesis of lactic acid from cellulose catalyzed by lead(II) ions in water", NatCommun, 2013, 4 (Ii), 2141, 7 pages.

Werpy et al., "Top Value Added Chemicals from Biomass: vol. I—Results of Screening for Potential Candidates from Sugars and Synthesis Gas", 2004, vol. 1, 76 pages.

Yanagihara et al., "Novel Branching of a Ketose Promoted by the Nickel(II)—Diamine Complex. The Isomerization of D-Fructose into D-Hamamelose", Chemistry Letters, 1992, No. 1, 89-90.

* cited by examiner

D-Fructose        D-Hamamelose

L-Sorbose        D-Tagatose        L-Psicose

PRODUCTION OF ALPHA-HYDROXY CARBOXYLIC ACIDS AND ESTERS FROM HIGHER SUGARS USING TANDEM CATALYST SYSTEMS

GOVERNMENT RIGHTS

This invention was made with government support under Grant No. DE-SC0001004/T-108118 awarded by the Department of Energy. The government has certain rights in the invention.

CROSS REFERENCE TO RELATED APPLICATIONS

This application claims the benefit of priority from U.S. Patent Application No. 62/194,069, filed Jul. 17, 2015, the contents of which are incorporated by reference herein for all purposes.

TECHNICAL FIELD

This application is related to the formation of alpha-hydroxy carboxylic acids and esters and intermediates from higher sugars.

BACKGROUND

Chemocatalytic routes for the production of α-hydroxy carboxylic acids (e.g. lactic acid, 2-hydroxy-3-butenoic acid, 2,4-dihydroxybutanoic acid, and glycolic acid) from biomass-derived sugars have been extensively studied in the recent years, as these acids, their esters, and lactones have been recognized to hold large potential as renewable, green platform chemicals for a number of industries (e.g. polymers, solvents, and fine chemicals).

Considerable progress has been made on the production of lactic acid and alkyl-lactates from trioses (glyceraldehyde (GLA) and dihydroxyacetone (DHA)), with nearly quantitative yields achievable with the state-of the art catalysts (e.g. tin containing zeotypes Sn-Beta and Sn-MFI, which catalyze 1,2 intramolecular hydride shift (1,2-HS) reactions) at moderate temperatures (ca. 100° C.) (FIG. 1). Similarly, the $C_4$- and $C_2$-products, 2-hydroxy-3-butenoic acid, 2,4-dihydroxybutanoic acid, and glycolic acid or their esters and/or lactones can be obtained in good yields when tetroses (erythrose, threose, and erythrulose), glycolaldehyde, or glyoxal are used as substrates (FIG. 2). However, the substrates required for these reactions are not easily obtained or isolated from biomass, as majority of terrestrial biomass comprises cellulose and hemicellulose (polymers of hexoses and pentoses).

SUMMARY

The present invention disclosure is directed to methods of preparing alpha-hydroxy carboxylic acids and esters, such as lactic acid and its esters, from higher sugars using coupled tandem catalysts. In certain of these embodiments, the methods comprise contacting a carbohydrate feedstock with such tandem catalyst system, the contacting resulting in the formation of an α-hydroxy carboxylic acid or α-hydroxy carboxylic acid ester, wherein the tandem catalyst system comprises:
(a) a first retro-aldol catalyst; and
(b) a second Lewis acid catalyst.

The carbohydrate feedstock includes any cellulosic and hemicellulosic biomass material, either as-provided or partially or completely hydrolyzed to its constituent oligo-, di-, or monosaccharides. In preferred embodiments, the feedstock is characterized as comprising at least one pentose or hexose monosaccharide. In other embodiments, the carbohydrate feedstock is characterized as comprising at least one aldose or ketose monosaccharide. Glucose, mannose, fructose, and xylose are only some of the materials useful in these disclosed methods.

These first and second catalysts may be described either functionally or chemically, or in both functional and chemical terms, and all of such descriptions are considered within the scope of the present disclosure.

In some embodiments, the retro-aldol catalyst is described as a material capable of performing the 1,2-carbon shift reaction on an aldose or ketose substrate, i.e.:

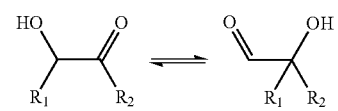

where $R_1$ is a carbohydrate chain, and $R_2$ is H or $CH_2OH$. Such a capability may be independently observed in the absence of the second Lewis acid catalyst. In other embodiments, the first retro-aldol catalyst may also be described as capable of converting a pentose or hexose monosaccharide to a diose, triose, or tetrose intermediate, with the elimination of glycolaldehyde or glyceraldehyde (see, e.g., FIGS. 1-4). In still other embodiments, the first retro-aldol catalyst is capable of effecting the 1,2-intramolecular carbon shift reaction of the pentose/hexose and is also capable of effecting retro-aldol reactions to as to form a diose/triose/tetrose intermediate.

The first retro-aldol catalyst may also be described by its chemical nature. In various embodiments, this catalyst comprises an optionally substituted oxo(hydroxy)molybdate, sulfomolybdate, or oxy(hydroxy)tungstate; a Ni(II) diamine complex; an alkali-exchanged hafno-, stanno-, titano-, or zirconosilicate; an optionally substituted amorphous $HfO_2$—, $SnO_2$—, $TiO_2$—, or $ZrO_2$—$SiO_2$ co-precipitate; or a combination thereof.

The Lewis acid catalyst is a material capable of performing the 1,2-hydride shift reaction on an aldose substrate, i.e.:

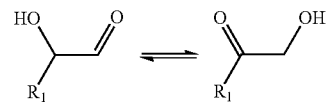

where $R_1$ is a carbohydrate chain. The second Lewis acid catalyst may also be described functionally as a catalyst capable of converting a diose, triose, or tetrose intermediate (e.g., as provided by the reaction of the retro-aldol catalyst with the appropriate feedstock) to an α-hydroxy carboxylic acid or α-hydroxy carboxylic acid ester. Again, such a capability may be independently observed in the absence of the first retro-aldol catalyst.

The second Lewis acid catalyst may also be described by its chemical nature. In its broadest context, the Lewis acid catalyst comprises any Lewis acid capable of effecting the transformation of functions attributed to it. In other various embodiments, this catalyst comprises one or more of a hafnium-, tin-, titanium-, or zirconium-substituted crystalline microporous silicate or zeolite, or an amorphous hafnium-, tin-, titanium-, or zirconium-silicate co-precipitate. In certain of these embodiments, crystalline microporous materials having pores equal to 10-MR or 12-MR (or larger) may be useful. While larger pore sized materials are within the scope of the present disclosure, 10-MR systems may have the potential to confer size selectivity for improved yields.

The reaction solvents of the disclosed methods do not appear to be particularly restricting, though polar solvents (either protic or aprotic) appear to be useful. Protic alcoholic solvents appear to work better than aqueous solvents, perhaps due to solubility and passivation considerations.

In addition to the methods described, the disclosure also considers those compositions used or derived from the methods as specific embodiments.

BRIEF DESCRIPTION OF THE DRAWINGS

The present application is further understood when read in conjunction with the appended drawings. For the purpose of illustrating the subject matter, there are shown in the drawings exemplary embodiments of the subject matter; however, the presently disclosed subject matter is not limited to the specific methods, processes, devices, and systems disclosed. In addition, the drawings are not necessarily drawn to scale. In the drawings.

DETAILED DESCRIPTION OF ILLUSTRATIVE EMBODIMENTS

The present invention may be understood more readily by reference to the following description taken in connection with the accompanying Figures and Examples, all of which form a part of this disclosure. It is to be understood that this invention is not limited to the specific products, methods, processes, conditions or parameters described or shown herein, and that the terminology used herein is for the purpose of describing particular embodiments by way of example only and is not intended to be limiting of any claimed invention. Similarly, unless specifically otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this specification, claims, and drawings, it is recognized that the descriptions refer to compositions and processes of making and using said compositions. That is, where the disclosure describes or claims a feature or embodiment associated with a composition, it is appreciated that such a description or claim is intended to extend these features or embodiment to embodiments to the method of making or using the composition, and vice versa—i.e., a feature described in one context is also applicable in all of these contexts (i.e., compositions, methods of making, and methods of using).

Figure 1:
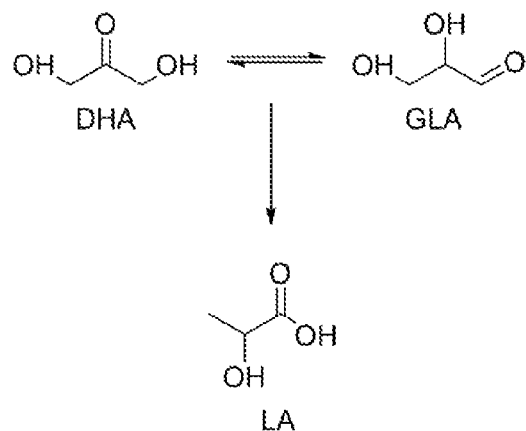
FIG. 1 schematically illustrates the formation of $C_3$ α-hydroxy carboxylic acids from trioses.
Figure 2:
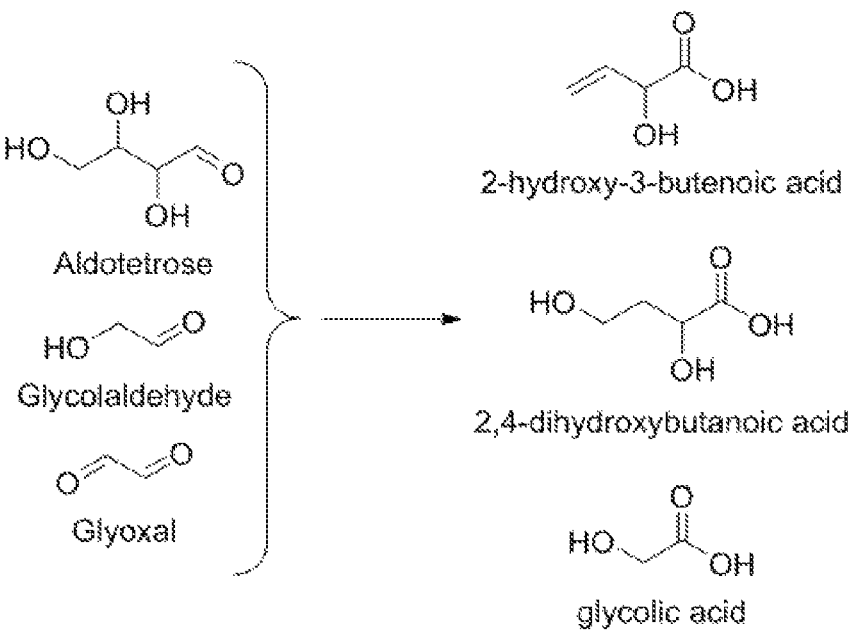
FIG. 2 schematically illustrates the formation of C4 and C2 α-hydroxy carboxylic acids from tetroses, glycolaldehyde, and glyoxal.
Figure 3:
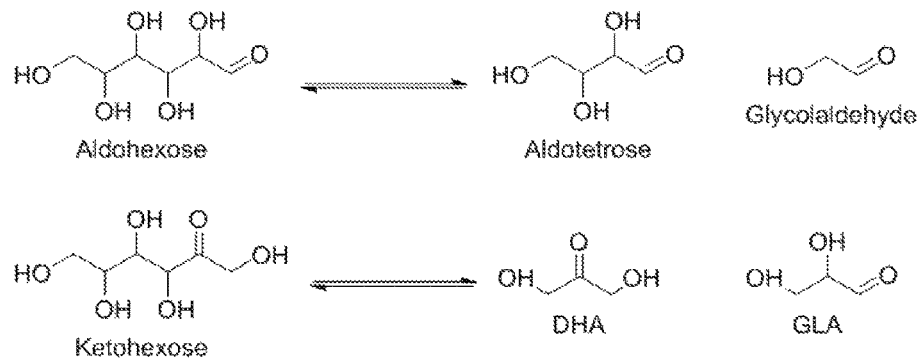
FIG. 3 schematically illustrates representative retro-aldol reactions of aldo- and keto-hexoses.
Figure 4:
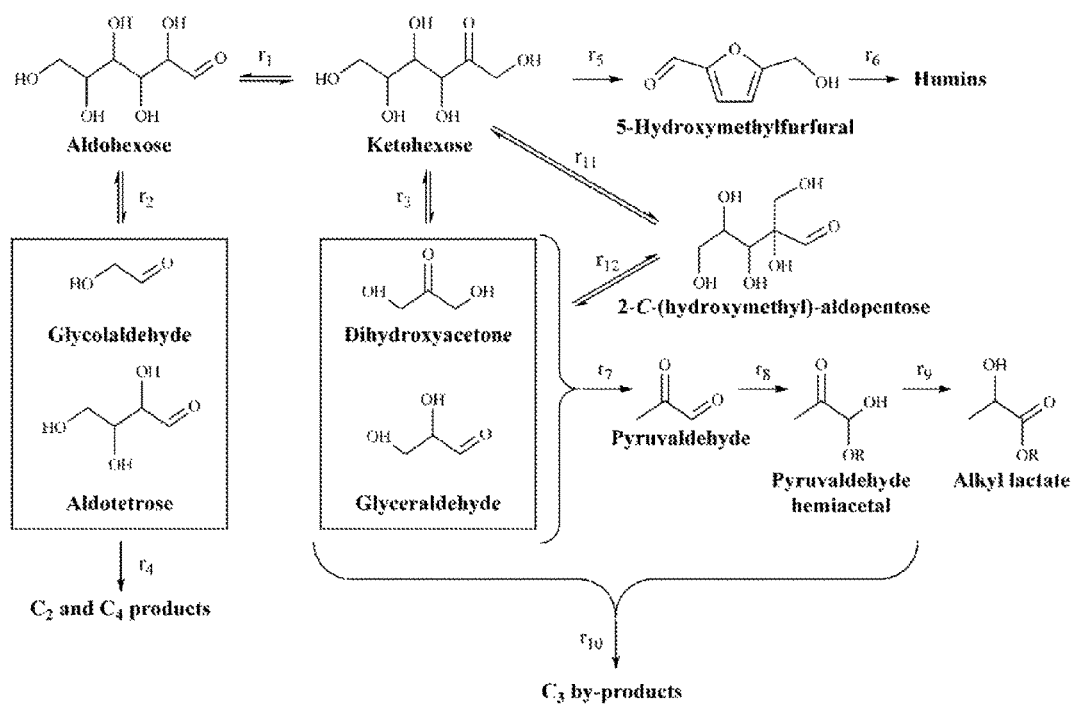
FIG. 4 schematically illustrates representative reaction network in which ketohexoses can isomerize to aldohexoses via 1,2-HS (r1) and to 2-C-(hydroxymethyl)-aldopentoses via 1,2-intramolecular carbon shift (1,2-CS) (r11) reactions. Retro-aldol reactions of hexose species (r2, r3, and r12) lead to the formation of C2, C3, and C4 carbohydrate fragments. Lewis acids can then catalyze the formation of α-hydroxy carboxylic acids from these smaller fragments (e.g., r7, r8, and r9 in the formation of alkyl lactate from trioses). Side reactions, involving dehydration reactions of fructose to 5-HMF (r5), redox and fragmentation reactions of unstable intermediates, and various humin-forming condensation reactions, lead to loss of yield of desired products.

The present disclosure is based on the recognition of the need to use retro-aldol reactions to fragment the larger sugars' carbon backbones (FIG. 3 and FIG. 4) to form these $C_2$-$C_4$ α-hydroxy carboxylic acids from hexoses and pentoses (e.g., r2 and r3 in FIG. 4). For the common aldo- and keto-hexoses and pentoses, these C—C bond-splitting reactions have large activation energies and unfavorable thermodynamics at low-to-moderate temperatures. As a result, most attempts at the catalytic production of $C_2$-$C_4$ α-hydroxy carboxylic acids from hexoses and pentoses have involved high temperature conditions (≥160° C.). Carbon-basis yields ca. 64-68% of methyl lactate at full conversion were reported for reactions of sucrose catalyzed by Sn-Beta at 160° C. for 20 h. Lower yields ca. 40-44% were reported for monosaccharide substrates in the same study. Similarly, lower yields of lactate products were reported for the reaction of sucrose in different solvents (39%, <30%, 25% for ethanol, water, and isopropanol, respectively). The Sn-Beta catalyst was shown to be reusable, but needed to be calcined between runs due to deposition of carbon that happens at high temperatures. Recently, methyl lactate yields upwards of 75% from sucrose with Sn-Beta at 170° C., when specific amounts of alkali carbonates were added to the reaction system. Again, the yields from monosaccharides were significantly lower.

Among the potential reasons for the carbon deposition on the catalyst and low selectivities in some solvents are the poor thermal stability of sugars beyond 100° C. and the lack of substrate and reaction specificity of the catalytic sites investigated in the aforementioned systems. Dehydration reactions of ketohexoses to 5-hydroxymethyl furfural (5-HMF) become prevalent at high temperatures (r5 in FIG. 4). The subsequent fragmentation and coupling reactions of 5-HMF can lead to the formation of insoluble humins that deposit on the catalyst, thereby leading to catalyst deactivation. Furthermore, large-pore catalysts like Sn-Beta can promote aldose-ketose isomerization reactions (r1 in FIG. 4) of substrates as large as disaccharides because the Lewis acid sites that are active for 1,2-HS reactions are accessible to such species. The same Lewis acid sites have been previously proposed as the active sites in retro-aldol reactions. As a result, Sn-Beta (and other 12-MR materials) does not readily allow for size-dependent discrimination among the substrates, and results in retro-aldol reaction happening on both aldo- and keto-hexoses, resulting in the concomitant formation of $C_2$ and $C_4$ products, in addition to the more desired $C_3$ products. That is, even when ketohexose substrates are used, $C_2$ and $C_4$ products derived from aldoses concomitantly form with the more desired $C_3$ products derived from ketoses (r4 and r7-r10 in FIG. 4, respectively). Because of these features, catalytic strategies that allow for retro-aldol reactions of hexoses to proceed in the absence of aldose-ketose isomerization would be highly useful, as they would have the potential to significantly affect the distribution of $C_2$, $C_3$, and $C_4$ products For these reasons, catalysts and catalytic strategies that allow for lower temperature retro-aldol reactions and tunability of accessible active site ratios for the retro-aldol and isomerization reactions are desired.

The present invention is directed to the preparation of alpha-hydroxy carboxylic acids and esters using catalytic systems comprising moderate-temperature (around 100° C.) retro-aldol reactions of various hexoses in aqueous and alcoholic media with catalysts traditionally known for their capacity to catalyze 1,2-intramolecular carbon shift (1,2-CS) reactions of aldoses. Because these catalysts do not readily catalyze aldose-ketose interconversion through 1,2-HS, they are candidate co-catalysts for reaction pathways that benefit from aldose- or ketose-specific, retro-aldol fragmentation. Here, these retro-aldol catalysts are combined with Lewis acid catalysts to enable the moderate-temperature conversion of hexoses into α-hydroxy carboxylic acids.

In this disclosure, various embodiments provide methods for the preparation of certain α-hydroxy carboxylic acid or α-hydroxy carboxylic acid esters, for example lactic acid or esters of 2-hydroxy-3-butenoic acid, 2,4-dihydroxybutanoic acid, glycolic acid, or esters thereof from carbohydrate feedstocks. In certain embodiments, the methods comprise contacting a carbohydrate feedstock with a tandem catalyst system, the contacting resulting in the formation of an α-hydroxy carboxylic acid or α-hydroxy carboxylic acid ester, wherein the tandem catalyst system comprises:

(a) a first retro-aldol catalyst; and
(b) a second Lewis acid catalyst.

In the present case, the methods are operable at temperatures of 200° C. or less, preferably 160° C. or less, more preferably about 100° C., to effect conversions to the extent as described in the Examples. In certain embodiments, the methods can be effected at temperatures defined by one or more ranges from 60° C. to 80° C., from 80° C. to 100° C., from 100° C. to 120° C., from 120° C. to 140° C., from 140° C. to 160° C., from 160 to 180° C., from 180° C. to 200° C., or higher. In order to maintain these temperatures with some of the contemplated solvents or solvent systems, the methods are typically done in sealed vessels, in which the pressures are those autogenous pressures associated with the systems.

The carbohydrate feedstock includes any cellulosic and hemicellulosic biomass material, either as-provided or partially or completely hydrolyzed to its constituent oligo-, di-, or monosaccharides. In some related embodiments, these methods further comprise hydrolyzing or otherwise treating (e.g., by alcoholysis) biomass so as to provide the constituent oligo-, di-, or monosaccharides or glycoside, glycophosphate, acetal, or hemiacetal derivatives thereof. In preferred of these, the treatment results in the formation of the monosaccharides. Alternatively, the methods use these constituent materials as provided from other sources. In preferred embodiments, the feedstock is characterized as comprising at least one pentose or hexose monosaccharide. The carbohydrate feedstock may also be characterized as comprising at least one aldose or ketose monosaccharide. As intended herein, aldose monosaccharides include one or more of ribose, arabinose, xylose, lyxose (pentoses) and allose, altrose, glucose, mannose, gulose, idose, talose, and galactose (hexoses). Similarly, the ketose monosaccharides include one or more of ribulose, xylulose (pentoses), fructose, psicose, sorbose, and tagatose (hexoses). Similarly, branched chain monomers, such as hamamelose, its stereoisomers, and/or pentose analogues, may be suitably used in these methods. Glucose, mannose, fructose, and xylose are especially attractive substrates for these methods.

The methods are described in terms of a "tandem catalyst system," which refers to the use of both first and second catalysts on a common feedstock and/or reaction mixture. In some embodiments, this refers to a comingled mixture of the first and second catalysts, both in a common vessel in a common reaction mixture and common solvent system. But in other embodiments, these catalysts may be applied separately/sequentially to a given feedstock, for example, in a recycle situation.

The first retro-aldol and second Lewis acid catalysts may be described either functionally or chemically, or in both functional and chemical terms, and all of such descriptions are considered within the scope of the present disclosure. Unless otherwise specified, the first and second catalysts perform comprise different discrete materials, the first acting as the retro-aldol catalyst and the second as the Lewis acid catalyst. However, when explicitly specified, a the first and second catalysts may be combined to provide a composite catalyst, wherein a single integrated composition comprises both types of materials. For example, a partially substituted a stannosilicate that is partially ion-exchanged may be seen as having both 1,2-HS and 1,2-CS/retro-aldol sites. Similarly, a stannosilicate (or other 1,2-HS catalyst) that is impregnated with a 1,2-CS catalyst (such as a MoOx species or Ni (II) diamine complexes) may provide such multifunctional, composite activity.

In some embodiments, the retro-aldol catalyst is described as a material capable of performing the 1,2-carbon shift reaction on an aldose or ketose substrate, i.e.:

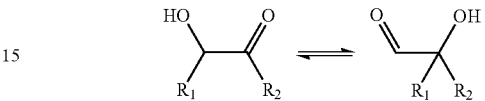

where $R_1$ is a carbohydrate chain, and $R_2$ is H or $CH_2OH$. Such a capability may be independently observed in the absence of the second Lewis acid catalyst. For example (referring to FIG. 3), for an exemplary aldose:

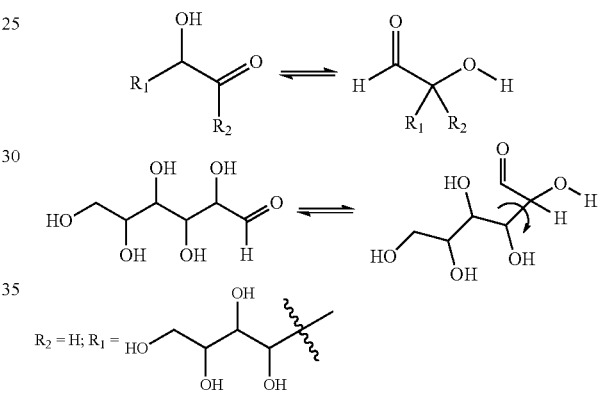

While not intending to be bound by the correctness of any particular theory, it is possible that this mechanism may act as a pre-step to the second retro-aldol reaction:

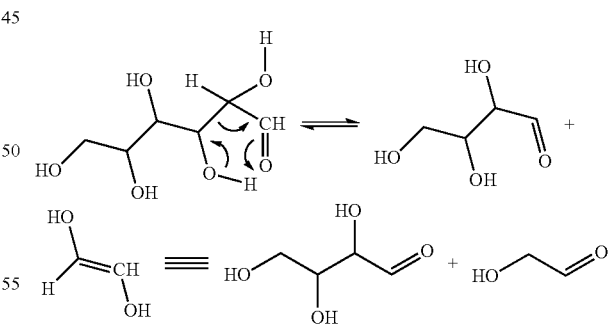

Similarly, for an exemplary ketose:

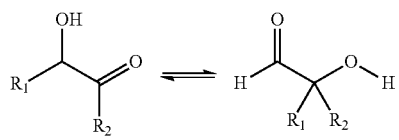

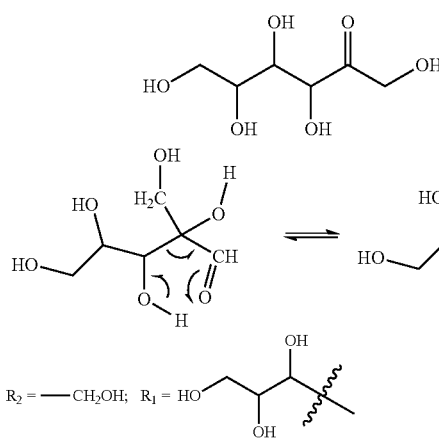 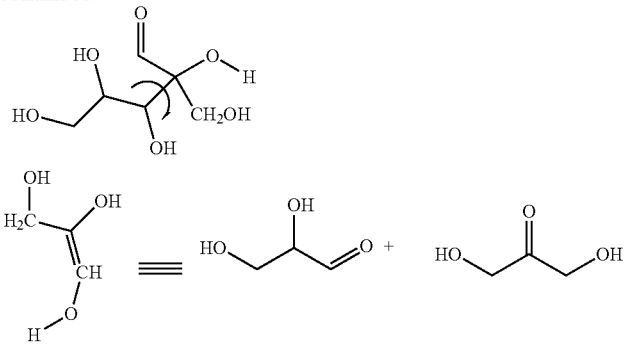

Alternatively, it is possible that the retro-aldol catalysts operates to enable the 1,2-carbon shift reaction in parallel with or through a common intermediate of the retro-aldol reaction. In some embodiments, the first retro-aldol catalyst may also be described as capable of converting a pentose or hexose monosaccharide to a diose, triose, or tetrose intermediate, for example with the elimination of glycolaldehyde or glyceraldehyde (see, e.g., FIGS. 1-4). In still other embodiments, the first retro-aldol catalyst is capable of effecting the 1,2-intramolecular carbon shift reaction of the pentose/hexose and is also capable of effecting retro-aldol reactions to as to form a diose/triose/tetrose intermediate.

In some embodiments, the first retro-aldol catalyst comprises an optionally substituted oxo(hydroxy)molybdate, sulfomolybdate, or oxy(hydroxy)tungstate; a Ni(II) diamine complex; an alkali-exchanged crystalline microporous hafno-, stanno-, titano-, or zirconosilicate; an optionally substituted amorphous hafnium-, tin-, titanium-, or zirconium-silicate co-precipitate; or a combination thereof. The active catalyst may be added to the reaction mixture as such, or as a precursor that is effective for the described purpose. These catalysts are known to be effective for the epimerization of the aldoses and for the rearrangement of ketoses to 2-C-hydroxymethyl aldoses, as described herein.

As used herein, the terms "oxo(hydroxy) molybdate" and "sulfomolybdate" include those complexes of molybdenum having oxo and optional hydroxy ligands and sulfide ligands, respectively; these are often complex polyanions in use, which may or may not be substituted with other elements, for example, $LiNbMoO_6$ and $HNbMoO_6$). In other specific embodiments, the first retro-aldol catalyst is either present as or derived from an oxomolybdate or sulfomolybdate precursor of $MoO_3$, $MoO_2$, $MoS_2$, $MoS_3$, $Mo_2S_5$, $MoO(OH)_2$, $MoO_4^{2-}$, $Mo_5O_{14}$, $Mo_2O_7^{2-}$, $Mo_{17}O_{47}$, $H_3PMo_{12}O_{40}$ (or other Keggin structures containing Mo), $[Mo_7O_{24}]^{6-}$, or a combination thereof. Again, the term "derived from" reflects the use of these materials, as added to the reaction mixture, which convert to active catalytic species during the course of the reaction. In many cases, the active materials have complex structures which may not be fully characterized. Where the materials are anions or polyanions, the materials may be added as ammonium, alkali metal, alkaline earth metal, or transition metal (e.g., zinc) salts. The catalysts may be soluble or insoluble salts or may be immobilized onto an anion exchange support, or on an inert surface, such as a solid oxide (e.g., silica).

In other embodiments, the first retro-aldol catalyst comprises a diamine complex of Ni(II), typically a bidentate diamine complex, and preferably an ethylenediamine complex of Ni(II). In some embodiments, the ethylenediamine complexes of Ni(II) include mono-, di-, tri-, or tetraalkyl ethylenediamine complexes of Ni(II), including nickel halides, for example Ni(II)(N,N,N',N'-tetramethylethylenediamine)$_2$Cl$_2$]

The Lewis acid catalyst is a material capable of performing the 1,2-hydride shift reaction on an aldose or ketose substrate, i.e.:

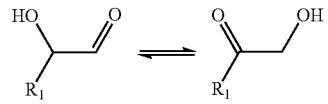

where $R_1$ is a carbohydrate chain. Again, such a capability may be independently observed in the absence of the first retro-aldol catalyst. The second Lewis acid catalyst may also be described functionally as a catalyst capable of converting a diose, triose, or tetrose intermediate (e.g., as provided by the reaction of the retro-aldol catalyst with the appropriate feedstock) to an α-hydroxy carboxylic acid (such as lactic acid) or α-hydroxy carboxylic acid ester (such as a lactic acid ester). In addition to lactic acid from trioses, 2-hydroxy-3-butenoic acid, 2,4-dihydroxybutanoic acid, and glycolic acid and their esters have been observed with diose and tetrose substrates reacting with 1,2-HS catalysts. See, e.g., M. Dusselier, et al., Chem Cat Chem 2013, 5 (2), 569-575 and P. Y. Dapsens, et al., Green Chem. 2014, 16 (3), 1176.

Again, without intending to be bound by the correctness of any particular theory, it is believed that the 1,2-HS is implicated in the formation of lactates as shown in the added schematic (R is H or alkyl group from alcohol solvent). See, e.g., P. P. Pescarmona, P. P., et al., Green Chem. 2010, 12 (6), 1083.

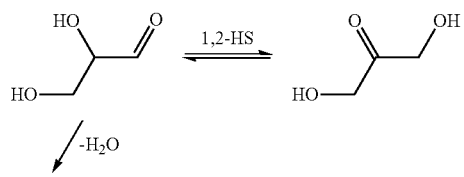

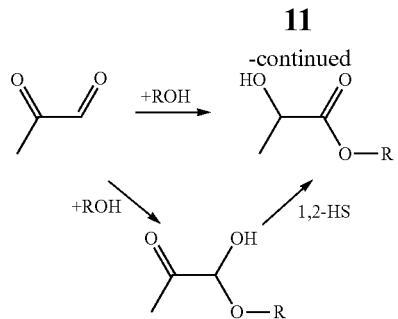

The second Lewis acid catalyst may also be described by its chemical nature. In its broadest context, in some embodiments, the Lewis acid catalyst comprises any Lewis acid capable of effecting the transformation of functions attributed to it. In certain embodiments, these Lewis acid catalysts are specifically devoid of Brønsted acidity. In other embodiments, the Lewis acid catalyst may exhibit some Brønsted acidity. The Lewis acid catalyst may be a heterogeneous catalyst or a soluble homogeneous catalyst, for example a Lewis acid salt. Lewis acid salts have been reported to enable the isomerization of trioses into lactates, so it is to be expected that such salts, which include but are not limited to aluminum, chromium, tin, or zinc salts such as $AlCl_3$, $Al_2(SO_4)_3$, $CrCl_2$, $CrSO_4$, $CrCl_3$, $SnCl_2$, $ZnSO_4$, may also be operable in the present tandem catalytic system; see, e.g., C. B. Rasrendra, et al., *Chem Sus Chem* 2011, 4 (6), 768-777, which is incorporated by reference herein at least for its teaching of the salts and reaction conditions. In other various embodiments, the second Lewis acid catalyst comprises a substituted crystalline microporous solid containing pores equal to or greater than 10-MR. In independent embodiments, the crystalline microporous solid contains 10-MR pores, 12-MR pores, or larger pores. In preferred embodiments, these crystalline microporous solids are alkali-free forms of these materials.

Crystalline microporous materials comprising 10-membered rings believed to be useful in this capacity include those having topologies of AEL (4.0×6.5 Å), AFO (4.3×7.0 Å), AHT (3.3×6.8 Å), CGF (2.5×9.2 Å), CGS (3.5×8.1 Å), DAC (3.4×5.3 Å), EUO (4.1×5.4 Å), FER (4.2×5.4 Å), HEU (3.1×7.5 Å), IMF (5.5×5.6 Å, 5.3×5.4 Å, 5.3×5.9 Å, 4.8×5.4 Å 5.1×5.3 Å), ITH (4.8×5.3 Å, 4.8×5.1 Å), LAU (4.0×5.3 Å), MEL (5.3×5.4 Å), MFI (5.1×5.5 Å, 5.3×5.6 Å), MFS (5.1×5.4 Å), MTT (4.5×5.2 Å), MWW (4.0×5.5 Å, 4.1×5.1 Å), NES (4.8×5.7 Å), OBW (5.0×5.0 Å), PAR (3.5×6.9 Å), PON (5.0×5.3 Å), RRO (4.0×6.5 Å), SFF (5.4×5.7 Å), SFG (5.2×5.7 Å, 4.8×5.7 Å), STF (5.4×5.7 Å), STI (4.7×5.0 Å), STW (5.9×5.9 Å), SZR (4.1×5.2 Å), TER (5.0×5.0 Å, 4.1×7.0 Å), TON (4.6×5.7 Å), TUN (5.6×5.5 Å, 5.4×5.5 Å), WEI (3.1×5.4 Å), and WEN (2.5×4.8 Å). Parenthetical pore sizes attributable to the topology come from the Ch. Baerlocher, *Atlas of Zeolite Framework Types*, Sixth Revised Edition, 2007, Structure Commission of the International Zeolite Association. In preferred embodiments, the crystalline microporous materials comprising 10-membered rings include those having MFI, MWW, MEI, and FER topologies.

Crystalline microporous materials comprising 1-membered rings believed to be useful in this capacity include those having topologies of AFI (7.3×7.3 Å), AFR (6.7×6.9 Å), AFS (7.0×7.0 Å), AFY (6.1×6.1 Å), ASV (4.1×4.1 Å), ATO (5.4×5.4 Å), ATS (6.5×7.5 Å), *BEA (6.6×6.7 Å, 5.6×5.6 Å), BEC (6.3×7.5 Å, 6.0×6.9 Å), BOG (7.0×7.0 Å), BPH (6.3×6.3 Å), CAN (5.9×5.9 Å), CON (6.4×7.0 Å, 7.0×5.9 Å), CZP (3.8×7.2 Å), DFO (7.3×7.3 Å, 6.2×6.2 Å), EMT (7.3×7.3 Å, 6.5×7.5 Å), EON (6.7×6.8 Å), EZT (6.5×7.4 Å), FAU (7.4×7.4 Å), GME (7.0×7.0 Å), GON (5.4×6.8 Å), IFR (6.2×7.2 Å), ISV (6.1×6.5 Å, 5.9×6.6 Å), IWR (5.8×6.8 Å), IWV (6.2×6.9 Å, 6.2×6 Å), IWW (6.0×6.7 Å), LTL (7.1×7.1 Å), MAZ (7.4×7.4 Å), MEI (6.9×6.9 Å), MOR (6.5×7.0 Å), MOZ (6.8×7.0 Å, 6.8×6.8 Å), MSE (6.4×6.8 Å), MTW (5.6×6.0 Å), NPO (3.3×4.4 Å), OFF (6.7×6.8 Å), OSI (5.2×6.0 Å), RON (4.3×4.3 Å), RWY (6.9×6.9 Å), SAO (6.5×7.2 Å, 7.0×7.0 Å), SBE (7.2×7.4 Å), SBS (6.8×6.8 Å, 6.9×7.0 Å), SBT (6.4×7.4 Å, 7.3×7.8 Å), SFE (5.4×7.6 Å), SFO (6.9×7.1 Å), SOS (3.9×9.1 Å), SSY (5.0×7.6 Å), USI (6.1×6.2 Å), and VET (5.9×5.9 Å). In preferred embodiments, the crystalline microporous materials comprising 12-membered rings include those having BEA, FAU, CON, AFI, and MOR topologies In the context of these frameworks, in some embodiments, the second solid Lewis acid catalyst comprises a crystalline microporous hafno-, stanno-, titano-, zirconosilicate, or mixed metal silicate. In other embodiments, the crystalline microporous hafno-, stanno-, titano-, or zirconosilicate is a hafno-, stanno-, titano-, or zirconozeolite. Again, in preferred embodiments, these crystalline microporous silicates or zeolites are alkali-free forms of these materials. In specific independent embodiments, as shown in the Examples, the crystalline microporous solid is a tin-substituted zeolite of MFI topology or a tin-substituted zeolite beta. Extra-framework aluminum Lewis acid sites have also been reported for the 1,2-HS, and are considered within the scope of the present invention.

In other embodiments, the Lewis Acid catalyst may also comprise a tin-, titanium-, zirconium-, and/or hafnium-containing amorphous silicate co-precipitates.

In the method reactions, the feedstocks, or their substrate components, are typically distributed within a solvent, preferably a polar solvent. In some embodiments, the solvent is protic, such as an alcohol or water. In other embodiment, the solvent is a polar aprotic solvent, such as acetonitrile, dimethylsulfoxide (DMSO), dimethylformamide (DMF), dimethylacetamide (DMA), hexamethylphosphoramide (HMPA), N-methyl pyrrolidone (NMP), a dioxane, a substituted furan, or an optionally tetrahydrofuran (e.g., 2-methyl furan or 2-methyl tetrahydrofuran). Ionic liquids may also be used in this capacity.

In some embodiments where the solvent comprises a protic solvent, that solvent is aqueous, containing water in a range of from 10 wt % to 100 wt % with respect to the total weight of the solvent. In other embodiments, the solvent is or comprises an alcohol, for example, one or more of a $C_{1-12}$ alcohol. The solvent may comprise a saturated, unsaturated, or aromatic alcohol. In certain preferred embodiments, the alcohol is at least one $C_{1-6}$ alcohol, for example a methyl, ethyl, propyl, butyl, pentyl, hexyl alcohol, or a mixture thereof. More preferably the alcohol is $C_{1-3}$ alcohol, i.e., methanol, ethanol, n-propanol, isopropanol, or a mixture thereof. In some embodiments, the solvent comprises an aqueous alcohol mixture. In other embodiments, the solvent comprising the one or more alcohols is anhydrous or substantially anhydrous, the term "substantially anhydrous" meanings that no water is deliberately added. Where specified, the term "substantially anhydrous" may also mean that deliberate steps are taken to remove adventitious water. Alcohol solvents appear to be preferred over aqueous solvents possible because of the poorer solubility of the retro-aldol catalysts, therein, relative to water. Alcohols may also be preferred due to reduction of passivation by coordination with alpha-hydroxy acids (because esters are formed instead.

While any and all of the various permutations of feedstocks, substrates, first and second catalysts, solvents and conditions are considered within the scope of the present invention, in certain specific embodiments, the methods comprise contacting the catalysts and substrates where:

(a) the carbohydrate feedstock comprises a C5 or C6 aldose or ketose monosaccharide;

(b) the first retro-aldol catalyst comprises an oxo(hydroxy)molybdate;

(c) the second Lewis acid catalyst comprises a Sn-beta or Sn-MFI zeolite; and (d) the tandem catalyst system further comprises an alcohol solvent;

wherein the method is operated under conditions so as to produce an α-hydroxy carboxylic acid or α-hydroxy carboxylic acid ester.

To this point, the present invention has been described in terms of the methods for preparing the α-hydroxy carboxylic acid or α-hydroxy carboxylic acid ester, the present disclosure also encompasses the associated compositions used or generated by these methods. For example, certain embodiments comprise:

(a) a carbohydrate feedstock as described in the context of any one of the preceding embodiments;

(b) a first retro-aldol catalyst as described in the context of any one of the preceding embodiments;

(c) a second Lewis acid catalyst as described in the context of any one of the preceding embodiments; and (d) optionally at least one α-hydroxy carboxylic acid or α-hydroxy carboxylic acid ester; and (e) optionally at least one aqueous or alcoholic solvent.

Representative embodiments of these compositions also include those described or evident from the Examples recited herein.

Terms

In the present disclosure the singular forms "a," "an," and "the" include the plural reference, and reference to a particular numerical value includes at least that particular value, unless the context clearly indicates otherwise. Thus, for example, a reference to "a material" is a reference to at least one of such materials and equivalents thereof known to those skilled in the art, and so forth.

When a value is expressed as an approximation by use of the descriptor "about" or "circa" (ca.), it will be understood that the particular value forms another embodiment. In general, use of the term "about" indicates approximations that can vary depending on the desired properties sought to be obtained by the disclosed subject matter and is to be interpreted in the specific context in which it is used, based on its function. The person skilled in the art will be able to interpret this as a matter of routine. In some cases, the number of significant figures used for a particular value may be one non-limiting method of determining the extent of the word "about." In other cases, the gradations used in a series of values may be used to determine the intended range available to the term "about" for each value. Where present, all ranges are inclusive and combinable. That is, references to values stated in ranges include every value within that range.

It is to be appreciated that certain features of the invention which are, for clarity, described herein in the context of separate embodiments, may also be provided in combination in a single embodiment. That is, unless obviously incompatible or specifically excluded, each individual embodiment is deemed to be combinable with any other embodiment(s) and such a combination is considered to be another embodiment. Conversely, various features of the invention that are, for brevity, described in the context of a single embodiment, may also be provided separately or in any sub-combination. Finally, while an embodiment may be described as part of a series of steps or part of a more general structure, each said step may also be considered an independent embodiment in itself, combinable with others.

The transitional terms "comprising," "consisting essentially of" and "consisting" are intended to connote their generally in accepted meanings in the patent vernacular; that is, (i) "comprising," which is synonymous with "including," "containing," or "characterized by," is inclusive or open-ended and does not exclude additional, unrecited elements or method or process steps; (ii) "consisting of" excludes any element, step, or ingredient not specified in the claim; and (iii) "consisting essentially of" limits the scope of a claim to the specified materials or steps "and those that do not materially affect the basic and novel characteristic(s)" of the claimed invention. Embodiments described in terms of the phrase "comprising" (or its equivalents), also provide, as embodiments, those which are independently described in terms of "consisting of" and "consisting essentially of" For those embodiments provided in terms of "consisting essentially of" the basic and novel characteristic(s) is the facile operability of the methods (or the systems used in such methods or the compositions derived therefrom) to convert a higher sugar to an α-hydroxy carboxylic acid, or ester or other derivative thereof.

When a list is presented, unless stated otherwise, it is to be understood that each individual element of that list, and every combination of that list, is a separate embodiment. For example, a list of embodiments presented as "A, B, or C" is to be interpreted as including the embodiments, "A," "B," "C," "A or B," "A or C," "B or C," or "A, B, or C."

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are described herein.

Throughout this specification, words are to be afforded their normal meaning, as would be understood by those skilled in the relevant art. However, so as to avoid misunderstanding, the meanings of certain terms will be specifically defined or clarified.

The term "aldose" carries its conventional meaning of a monosaccharide (a simple sugar) that contains only one aldehyde (—CH=O) group per molecule. The chemical formula takes the form $C_n(H_2O)_n$. The simplest possible aldose is the diose glycolaldehyde, which only contains two carbon atoms. Examples of aldose include glycolaldehyde (a diose), glyceraldehyde (a triose), erythrose, threose (tetroses), ribose, arabinose, xylose, lyxose (pentoses), allose, altrose, glucose, mannose, gulose, idose, talose, and galactose (hexoses). Similarly, the term "ketose" is also a monosaccharide containing a single ketone group. Examples of ketose include dihydroxyacetone (a triose), erythrulose (a tetrose), ribulose, xylulose (pentoses), fructose, psicose, sorbose, tagatose (hexoses), and sedoheptulose (a heptose).

Unless otherwise indicated, the term "isolated" means physically separated from the other components so as to be free of solvents or other impurities; additional embodiments include those where the compound is substantially the only solute in a solvent or solvent fraction, such a analytically separated in a liquid or gas chromatography phase.

As used herein, the terms "methods" or "processes" may be used interchangeably.

The term "microporous," according to IUPAC notation refers to a material having pore diameters of less than 2 nm. Similarly, the term "macroporous" refers to materials having pore diameters of greater than 50 nm. And the term "mesoporous" refers to materials whose pore sizes are intermediate between microporous and macroporous. Within the context of the present disclosure, the material properties and applications depend on the properties of the framework such as pore size and dimensionality, cage dimensions and material composition. Due to this there is often only a single framework and composition that gives optimal performance in a desired application.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present. Similarly, the phrase "optionally isolated" means that the target molecule or other material may or may not be separated from other materials used or generated in the method, and, thus, the description includes separate embodiments where the target molecule or other material is separated and where the target molecule or other material is not separated, such that subsequence steps are conducted on isolated or in situ generated product.

The terms "separating" or "separated" carries their ordinary meaning as would be understood by the skilled artisan, insofar as it connotes separating or isolating the material (e.g., terephthalic acid or ester) from other starting materials or co-products or side-products (impurities) associated with the reaction conditions yielding the material. As such, it infers that the skilled artisan at least recognizes the existence of the product and takes specific action to separate or isolate it. Absolute purity is not required, though preferred, as the material may contain minor amounts of impurities and the separated or isolated material may contain residual solvent or be dissolved within a solvent used in the reaction or subsequent purification of the material.

As used herein, the term "crystalline microporous solids" or "crystalline microporous silicates" are crystalline structures having very regular pore structures of molecular dimensions, i.e., under 2 nm. The maximum size of the species that can enter the pores of a crystalline microporous solid is controlled by the dimensions of the channels.

The term "silicate" refers to any composition including silicate (or silicon oxide) within its framework. It is a general term encompassing, for example, pure-silica (i.e., absent other detectable metal oxides within the silicate framework), aluminosilicate, borosilicate, ferrosilicate, stannosilicate, titanosilicate, or zincosilicate structures. The term "zeolite" refers to an aluminosilicate composition that is a member of this family. The term "aluminosilicate" refers to any composition including silicon and aluminum oxides within its framework. In some cases, either of these oxides may be substituted with other oxides. When described as "optionally substituted," the respective framework may contain aluminum, boron, gallium, germanium, hafnium, iron, tin, titanium, indium, vanadium, zinc, zirconium, or other atoms substituted for one or more of the atoms not already contained in the parent framework. Typically, the aluminum and other metals are tetrahedrally located within the framework, providing Lewis acidity to the framework. Where an oxide is described as being "extra-framework" (as in extra-framework aluminum Lewis acid sites), those oxides are positioned within the framework but not part of the crystalline framework structure.

The term "substantially anhydrous" in the context of solvents means that no water has been deliberately added. Where specified, the term "substantially anhydrous" may also mean that deliberate steps are taken to remove adventitious water.

The following listing of embodiments is intended to complement, rather than displace or supersede, the previous descriptions.

Embodiment 1

A method comprising contacting a carbohydrate feedstock with a tandem catalyst system, the contacting resulting in the formation of an α-hydroxy carboxylic acid or α-hydroxy carboxylic acid ester, wherein the tandem catalyst system comprises:

(a) a first retro-aldol catalyst; and
(b) a second Lewis acid catalyst.

In certain Aspects of this Embodiment, the retro-aldol catalyst is capable of performing the 1,2-carbon shift reaction on an aldose or ketose substrate, i.e.:

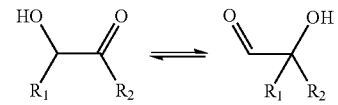

where $R_1$ is a carbohydrate chain, and $R_2$ is H or $CH_2OH$. In other Aspects of this Embodiment, the Lewis acid catalyst is capable of performing the 1,2-hydride shift reaction on an aldose substrate, i.e.:

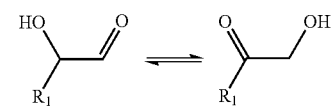

where $R_1$ is a carbohydrate chain.

Embodiment 2

The method of Embodiment 1, wherein the carbohydrate feedstock comprises a pentose or hexose monosaccharide.

Embodiment 3

The method of Embodiment 1 or 2, wherein carbohydrate feedstock comprises an aldose or ketose monosaccharide. In certain independent Aspects of this Embodiment, the aldose monosaccharides includes ribose, arabinose, xylose, lyxose (pentoses) and allose, altrose, glucose, mannose, gulose, idose, talose, and galactose (hexoses). In other independent Aspects of this Embodiments, the ketose monosaccharides includes one or more of ribulose, xylulose (pentoses), fructose, psicose, sorbose, and tagatose (hexoses)

Embodiment 4

The method of any one of Embodiments 1 to 3, wherein carbohydrate feedstock comprises glucose, mannose, fructose, psicose, sorbose, tagatose, or a combination thereof.

Embodiment 5

The method of any one of Embodiments 1 to 4, wherein the first retro-aldol catalyst comprises a catalyst capable of converting a pentose or hexose monosaccharide to a diose, triose, or tetrose intermediate.

Embodiment 6

The method of any one of Embodiments 1 to 5, wherein the first retro-aldol catalyst comprises an optionally substituted oxo(hydroxy)molybdate, sulfomolybdate, or oxy(hydroxy)tungstate; a Ni(II) diamine complex; an alkali-exchanged hafno-, stanno-, titano-, or zirconosilicate; an optionally substituted amorphous hafnium-, tin-, titanium-, or zirconium-silicate co-precipitate; or a combination thereof.

Embodiment 7

The method of any one of Embodiments 1 to 6, wherein the first retro-aldol catalyst is derived from an oxomolybdate or sulfomolybdate precursor of $MoO_3$, $MoO_2$, $MoS_2$, $MoS_3$, $Mo_2S_5$, $MoO(OH)_2$, $MoO_4^{2-}$, $Mo_5O_{14}$, $Mo_2O_7^{2-}$, $Mo_{17}O_{47}$, $H_3PMo_{12}O_{40}$, $[Mo_7O_{24}]^{6-}$, or a combination thereof. In certain Aspects of this Embodiment, the catalysts are either soluble or insoluble salts or may be immobilized onto an anion exchange support.

Embodiment 8

The method of any one of Embodiments 1 to 6, wherein the first retro-aldol catalyst comprises an ethylenediamine complex of Ni(II).

Embodiment 9

The method of any one of Embodiments 1 to 8, wherein the second Lewis acid catalyst comprises a catalyst capable of converting a diose, triose, or tetrose intermediate to an α-hydroxy carboxylic acid or α-hydroxy carboxylic acid ester.

Embodiment 10

The method of any one of Embodiments 1 to 9, wherein the second Lewis acid catalyst comprises a crystalline microporous solid containing pores equal to or greater than 10-MR. In certain Aspects of this Embodiment, the crystalline microporous solid containing 10-MR pores. In other Aspects of this Embodiment, the crystalline microporous solid containing 12-MR pores. Other Aspects of this Embodiment include those crystalline microporous materials comprising 10- and 12-membered rings described elsewhere herein.

Embodiment 11

The method of any one of Embodiments 1 to 10, wherein the second Lewis acid catalyst comprises a crystalline microporous hafno-, stanno-, titano-, or zirconosilicate. In certain Aspects of this Embodiment, the crystalline microporous hafno-, stanno-, titano-, or zirconosilicate is a hafno-, stanno-, titano-, or zirconozeolite. In other Aspects of this Embodiment, the crystalline microporous solid is a tin-substituted zeolite of MFI topology. In other Aspects of this Embodiment, the crystalline microporous solid is a tin-substituted zeolite beta.

Embodiment 12

The method of any one of Embodiments 1 to 11, where in the tandem catalyst system is or comprises a composite catalyst, the composite catalyst comprising having both the first retro-aldol catalyst and the second Lewis acid catalyst. In some Aspects of this Embodiment, the composite catalyst comprises the chemicals associated with the first and second catalysts.

Embodiment 13

The method of any one of Embodiments 1 to 12, wherein the tandem catalyst system comprises polar solvent. In certain Aspects of this Embodiment, the solvent is protic, such as an alcohol; in other Aspects, the solvent is aprotic, such as DMSO, dimethylsulfoxide (DMSO), dimethylformamide (DMF), dimethylacetamide (DMA), a dioxane, or an optionally substituted furan.

Embodiment 14

The method of any one of Embodiments 1 to 13, wherein the tandem catalyst system comprises an alcohol solvent. In some Aspects of this Embodiment, the solvent comprises a $C_{1-12}$ alcohol, preferably a $C_{1-6}$ alcohol, more preferably a $C_{1-3}$ alcohol.

Embodiment 15

The method of Embodiment 14, wherein the alcoholic solvent is substantially anhydrous.

Embodiment 16

The method of any one of Embodiments 1 to 14, wherein the tandem catalyst system comprises an aqueous solvent.

Embodiment 17

The method of any one of Embodiments 1 to 16, wherein
(a) the carbohydrate feedstock comprises a C5 or C6 aldose or ketose monosaccharide;
(b) the first retro-aldol catalyst comprises an oxo(hydroxy)molybdate;
(c) the second Lewis acid catalyst comprises a Sn-beta or Sn-MFI zeolite; and
(d) the tandem catalyst system further comprises an alcohol solvent;
wherein the method is operated under conditions so as to produce an α-hydroxy carboxylic acid or α-hydroxy carboxylic acid ester.

Embodiment 18

A composition comprising:
(a) a carbohydrate feedstock as described in the context of any one of the preceding Embodiments;

(b) a first retro-aldol catalyst as described in the context of any one of the preceding Embodiments;

(c) a second Lewis acid catalyst as described in the context of any one of the preceding Embodiments; and (d) optionally at least one α-hydroxy carboxylic acid or α-hydroxy carboxylic acid ester derived from any one of the reactions described herein; and (e) optionally at least one aqueous or alcoholic solvent.

EXAMPLES

The following Examples are provided to illustrate some of the concepts described within this disclosure. While each Example is considered to provide specific individual embodiments of composition, methods of preparation and use, none of the Examples should be considered to limit the more general embodiments described herein.

In the following examples, efforts have been made to ensure accuracy with respect to numbers used (e.g. amounts, temperature, etc.) but some experimental error and deviation should be accounted for. Unless indicated otherwise, temperature is in degrees C., pressure is at or near atmospheric.

Example 1. Materials and Methods

Example 1.1. Sources of Materials $MoO_3$ (Alfa Aesar, 99.95%), $MoO_2$ (Sigma-Aldrich, 99%), $H_3PMo_{12}O_{40} \cdot xH_2O$ (Alfa Aesar), $MoS_2$ (Alfa Aesar, 99%), $Na_2MoO_4$ (Sigma-Aldrich, 98%), $(NH_4)_6Mo_7O_{24} \cdot 4H_2O$ (Alfa Aesar, 99%), $NiCl_2 \cdot 6H_2O$ (Sigma-Aldrich, ≥98%), N,N,N',N'-tetramethylethylenediamine, (Alfa Aesar, 99%), D-fructose (Sigma-Aldrich, ≥99%), L-sorbose (Sigma-Aldrich, ≥98%), D-tagatose (Sigma-Aldrich, ≥98.5%), D-psicose (Sigma-Aldrich, ≥95%), D-hamamelose (Sigma-Aldrich, ≥99.5%), D-Glucose (Sigma-Aldrich, ≥98%), D/L-glyceraldehyde (Sigma-Aldrich, ≥90%), dihydroxyacetone dimer (Alfa Aesar, ≥70%), lactic acid (Sigma-Aldrich, ≥98%), methyl lactate (Sigma-Aldrich, ≥98%), ethyl lactate (Sigma-Aldrich, ≥99%), ethanol (Koptec, anhydrous 200-proof), methanol (Sigma-Aldrich, 99.8%), naphthalene (Sigma-Aldrich, 99%), tetraethylammonium hydroxide solution (Sigma-Aldrich, 35% in water), tetraethylorthosilicate (Sigma-Aldrich, 98% (w/w)), tin (IV) chloride pentahydrate (Sigma-Aldrich, 98%), hydrofluoric acid (Sigma Aldrich, 54% (w/w) in water), tetraethylammonium fluoride dihydrate (Sigma-Aldrich, 97%), $NaNO_3$ (Sigma Aldrich, ≥99.0%), NaOH (Alfa Aesar 97%) were purchased and used as received. Chloride form of Amberlite IRA-400 (Sigma-Aldrich) resin was used for immobilization of molybdate salts. $TiO_2$—$SiO_2$ co-precipitate (type III, No. 2) was obtained from W. R. Grace (Si/Ti=56) and was calcined in flowing air (100 mL min-1, Air Liquide, breathing grade) at 580° C. (ramped up at 1° C. min-1) for 6 h prior to use.

Example 1.2. Syntheses of Materials

Sn-MFI and Sn-Beta were synthesized according to previously reported procedures. The as-synthesized solids were centrifuged, washed extensively with water, and dried at 100° C. overnight. The dried solids were calcined in flowing air (100 mL min$^{-1}$, Air Liquide, breathing grade) at 580° C. (ramped up at 1° C. min$^{-1}$) for 6 h.

Example 1.2.1. Synthesis of Sn-Beta

Sn-Beta was synthesized as follows: 15.25 g of tetraethylammonium hydroxide solution (35% (w/w) in water) were added to 14.02 g of tetraethylorthosilicate, followed by the addition of 0.172 g of tin (IV) chloride pentahydrate. The mixture was stirred until tetraethylorthosilicate was completely hydrolyzed and then allowed to reach the targeted H2O:SiO2 ratio by complete evaporation of ethanol and partial evaporation of water. Next, 1.53 g of hydrofluoric acid (54% (w/w) in water) were added, resulting in the formation of a thick gel. The final molar composition of the gel was 1 $SiO_2$/0.0077 $SnCl_4$/0.55 TEAOH/0.54 HF/7.52 H2O. As-synthesized Si-Beta (vide infra) was added as seed material (5 wt % of $SiO_2$ in gel) to this gel and mixed. The final gel was transferred to a Teflon-lined stainless steel autoclave and heated at 140° C. in a static oven for 25 days. The recovered solids were centrifuged, washed extensively with water, and dried at 100° C. overnight. The dried solids were calcined in flowing air (100 mL min$^{-1}$, Air Liquide, breathing grade) at 580° C. (ramped up at 1° C. min$^{-1}$) for 6 h.

Example 1.2.2. Synthesis of Si-Beta

Si-Beta was synthesized as follows: 4.95 g of tetraethylammonium fluoride dihydrate was added to 10.00 g of water and 10.01 g of tetraethylorthosilicate. The mixture was stirred until tetraethylorthosilicate was completely hydrolyzed and then allowed to reach the targeted $H_2O$:$SiO_2$ ratio by complete evaporation of ethanol and partial evaporation of water. The final molar composition of the gel was 1 $SiO_2$/0.55 TEAF/7.25 $H_2O$. The gel was transferred to a Teflon-lined stainless steel autoclave and heated at 140° C. in a rotation oven (60 rpm) for 7 days. The solids were recovered by filtration, washed extensively with water, and dried at 100° C. overnight. The dried solids were calcined in flowing air (100 mL min$^{-1}$, Air Liquide, breathing grade) at 580° C. (ramped up at 1° C. min$^{-1}$) for 6 h.

Example 1.2.3. Synthesis of Sn-MFI

Sn-MFI was synthesized as follows: 0.92 g of tin (IV) chloride pentahydrate in 6.08 g of water added to 28.00 g of tetraethylorthosilicate and stirred (uncovered) for 30 min. Next, 48.21 g of tetrapropylammonium hydroxide solution (25% (w/w) in water) was added to the mixture under stirring. After 1 h of additional stirring (uncovered), the remaining water was added, to achieve the final molar composition of the gel of 1 $SiO_2$/0.02 $SnCl_4$/0.45 TPAOH/35$H_2O$. The gel was stirred for an additional 30 min (covered), evenly split among three Teflon-lined stainless steel autoclaves, and heated at 160° C. in a static oven for 48 h. The solids were recovered by filtration, washed extensively with water, and dried at 100° C. overnight. The dried solids were calcined in flowing air (100 mL min$^{-1}$, Air Liquide, breathing grade) at 580° C. (ramped up at 1° C. min$^{-1}$) for 6 h.

Example 1.2.4. Na-Exchange of Sn-Beta

Three successive sodium ion exchanges were performed according to previously described procedure (3) as follows: calcined Sn-Beta was stirred in a solution of 1 M $NaNO_3$ and 10-4 M NaOH in distilled water. Each ion exchange step was carried out for 24 hours at ambient temperature, using 45 mL of exchange or wash solution per 300 mg of starting solids. The material was recovered by centrifugation, and washed three times with 1 M $NaNO_3$ in distilled water. The final material was dried at ambient temperature overnight by an impinging flow of air.

Example 1.2.4. $H_3PW_{12}O_{40}$ and $(NH_4)_6Mo_7O_{24}$ Exchanged Resins $H_3PW_{12}O_{40}$ and $(NH_4)_6Mo_7O_{24}$ were immobilized by ion exchanging the chloride form of Amberlite IRA-400. In each procedure, n meq of ion capacity worth of resin was used per 1 meq of anion to be immobilized, where n is the charge of the anion. The resin was suspended in an aqueous solution of anion for 24 h, filtered, washed extensively with water, and dried at ambient temperature overnight by an impinging flow of air.

Example 1.3. Reaction Analyses

Carbohydrate analysis and fractionation were performed via high performance liquid chromatography on an Agilent 1200 system equipped with refractive index and evaporative light scattering detectors. An Agilent Hi-Plex Ca column held at 80° C. was used with ultrapure water as the mobile phase (flow rate of 0.6 mL min$^{-1}$).

Quantitative GC/FID analysis of alkyl lactates was performed on an Agilent 7890B GC system equipped with a flame ionization detector and an Agilent HP-5 column. Qualitative GC/MS analysis of side-products was performed on an Agilent 5890 GC system with an Agilent 5970 mass spectrometer and an Agilent DB-5 column.

Liquid $^1H$ and $^{13}C$ NMR spectra were recorded with a Varian INOVA 500 MHz spectrometer equipped with an auto-x pfg broad band probe. All liquid NMR analysis was performed in $D_2O$ solvent, with 4,4-dimethyl-4-silapentane-1-sulfonic acid (DSS) as an internal standard.

1.6

Reactions were performed in 10 mL thick-walled crimp-sealed glass reactors (VWR) that were heated in a temperature-controlled oil bath. A typical reaction procedure involved: addition of desired amount of catalysts (i.e. $MoO_3$, Sn-MFI, etc.), carbohydrate substrate (i.e. D-fructose, DHA, etc.), and solvent (i.e. EtOH, MeOH, etc. with pre-dissolved naphthalene as internal standard) to reactor, sealing of reactor with crimp-top, agitation of reactor at ambient temperature until dissolution of substrate, and placement of reactor in the oil bath at desired temperature. Aliquots (~100 µL) were extracted at indicated times, filtered with a 0.2 µm PTFE syringe filter, and analyzed by GC/FID. For reactions with [Ni(N,N,N',N'-Me$_4$en)$_2$]Cl$_2$, aliquots were agitated with 20 mg of Dowex 50WX2 (hydrogen form) resin to remove nickel (II) species prior to filtration. For product identification by HPLC, liquid NMR, or GC/MS, internal standard was excluded and the entire reactor content was used. Rotary evaporation was used to remove solvent when needed.

Example 2. Results and Discussions

Retro-aldol reactions of hexoses and pentoses were observed to proceed in alcoholic and aqueous media at moderate temperatures (ca. 100° C.) with catalysts traditionally known for their capacity to catalyze 1,2-intramolecular carbon shift reactions of aldoses (e.g. various molybdenum and tungsten oxide and molybdate and tungstate species, nickel (II) diamine complexes, alkali-exchanged stannosilicate molecular sieves, and amorphous $TiO_2$—$SiO_2$ co-precipitates). Products consistent with aldol recombination reactions were observed, and were attributed to unfavorable thermodynamics for retro-aldol reactions at temperatures and concentrations considered in this study. Co-catalysts (e.g. Lewis-acidic zeotypes and Lewis acids on amorphous supports) that are known to catalyze the formation of α-hydroxy carboxylic acids (e.g. lactic acid, 2-hydroxy-3-butenoic acid, 2,4-dihydroxybutanoic acid, and glycolic acid) and their esters and lactones from tetroses, trioses, and glycolaldehyde, but cannot readily catalyze retro-aldol reactions of hexoses and pentoses at these moderate temperatures, were shown to be compatible with the aforementioned retro-aldol catalysts.

The reported strategy of using a combination of distinct retro-aldol catalysts (e.g. $MoO_3$) and 1,2-intramolecular hydride shift catalysts (e.g. Sn-MFI) is a novel approach to lactic acid and alkyl lactate formation from ketohexoses. This method allows for lactate species formation at considerably lower temperatures (ca. 100° C.) and consequently pressures (autogenous) than previously reported methods, with yields comparable to the best-reported examples. Additionally, the Sn-MFI catalyst used in this study was synthesized in the absence of fluoride (a frequently raised concern for large scale synthesis of catalysts used in the previous studies of alkyl lactate formation from hexoses e.g. Sn-Beta). In principle, even more economically accessible catalysts that can catalyze lactate formation from trioses may be paired with the retro-aldol catalysts reported in this study.

Figure 5:
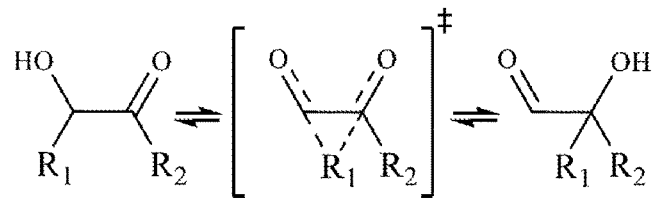
FIG. 5 is a schematic representation of a 1,2-CS($R_2$=H for aldoses or $R_2$=$CH_2OH$ for ketoses, and $R_1$ represents the remainder of the saccharide) that involves simultaneous breaking and forming of C—C bonds.
Figure 6:
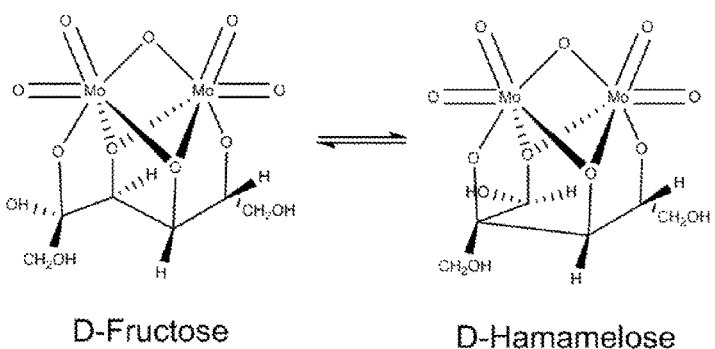
FIG. 6 illustrates a schematic representation of the stereospecific molybdate-catalyzed isomerization of D-fructose to D-hamamelose.

During recent investigation of epimerization reactions of aldohexoses on alkali-exchanged Sn-Beta materials, a change in the reaction pathway from a 1,2-intramolecular hydride shift (1,2-HS) to a 1,2-intramolecular carbon shift (1,2) upon alkali exchange was observed. This 1,2-CS pathway in aldohexoses (e.g., for the formation of mannose from glucose) is analogous to those previously reported for molybdate- and nickel(II) diamine-catalyzed reactions of these aldoses (also known as Bilik reaction), where simultaneous C—C bond-breaking and -forming steps were proposed to occur (FIG. 5). This reaction mechanism is analogous to the previously reported molybdate and nickel (II) diamine catalyzed reactions. Ketoses were observed to react through analogous pathways to form branched sugars (2-C-(hydroxymethyl)-aldoses) (FIG. 6 and r11 in FIG. 4). In addition to the branched sugars, small amounts of ketose isomers were observed (e.g. when D-fructose was reacted with molybdate, the branched sugar D-hamamelose formed, as well as small quantities of ketose isomers: sorbose, psicose, and tagatose). The formation of ketose isomers was attributed to competing hydride shift side reactions.

Here, the same branched sugar (D-hamamelose) and ketose isomers were observed when fructose was used as a substrate at temperatures ca. 100° C., with alkali-exchanged Sn-Beta as catalysts. In addition, small quantities of retro-aldol products, DHA and GLA, were observed in the HPLC chromatograms and NMR spectra of unseparated reaction solutions. The presence of DHA and GLA raised questions about the mechanism of ketose isomer formation, as it was possible to form all of the ketohexoses through non-stereospecific aldol condensation of DHA and racemic GLA. When water-dissolved $MoO_3$ was tested for similar products, when fructose was reacted at 100° C., initial formation of hamamelose, DHA, and GLA was observed. Subsequently, sorbose, tagatose, and psicose began to form, without a significant change in the DHA and GLA concentration. Quantification of products was not performed due to a multitude of partially overlapping peaks in HPLC chromatograms and NMR spectra, however, fructose and sorbose were eventually observed in substantially greater quantities than tagatose, psicose, and hamamelose. Fractionation of product solutions and NMR were used to confirm the presence of DHA, GLA, fructose, sorbose, tagatose, psicose, and 2-C-(hydroxymethyl)-aldopentoses (FIGS. 8-13). These results suggested that some of the ketose isomers may form as aldol condensation products of DHA and GLA, rather than directly from fructose through hydride shift reactions, as previously hypothesized. The unfavorable equilibrium of retro-aldol reactions at these moderate temperatures may be responsible for the low concentrations of DHA and GLA. The reverse reaction, aldol coupling, was a logical secondary reaction that can form the more stable ketohexose side-products. The possibility of aldol coupling was confirmed by reacting a mixture of DHA and GLA under the same conditions, resulting in the formation of ketohexoses and 2-C-(hydroxymethyl)-aldopentoses. Again, fructose and sorbose appeared as major detectable hexose products.

Figure 7:
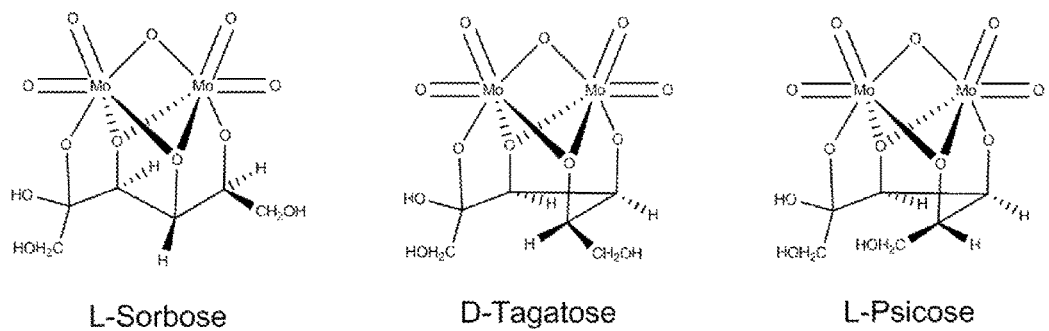
FIG. 7 illustrates structures of sorbose, tagatose, and psicose structural analogues of tetradentate molybdate complex of fructose hypothesized to be involved in isomerization to hamamelose.
Figure 8:
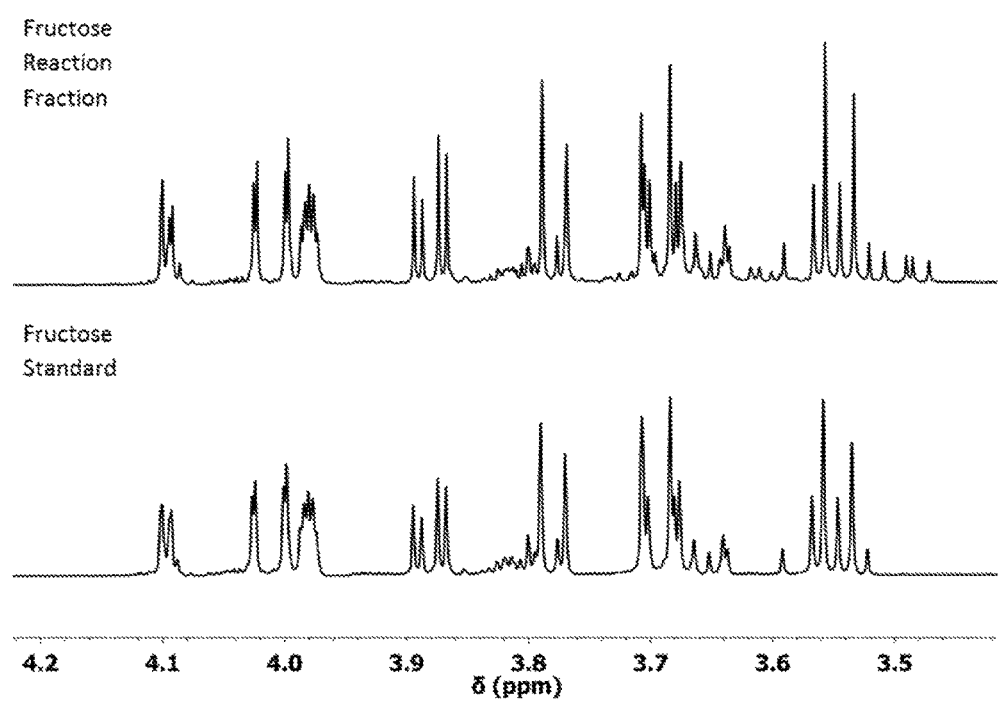
FIG. 8 shows $^1H$ NMR spectra of D-fructose standard solution and of the fructose-containing fraction isolated after reaction of D-fructose with $MoO_3$ in water at 100° C. for 4 h. Sorbose is present in the collected fraction.
Figure 9:
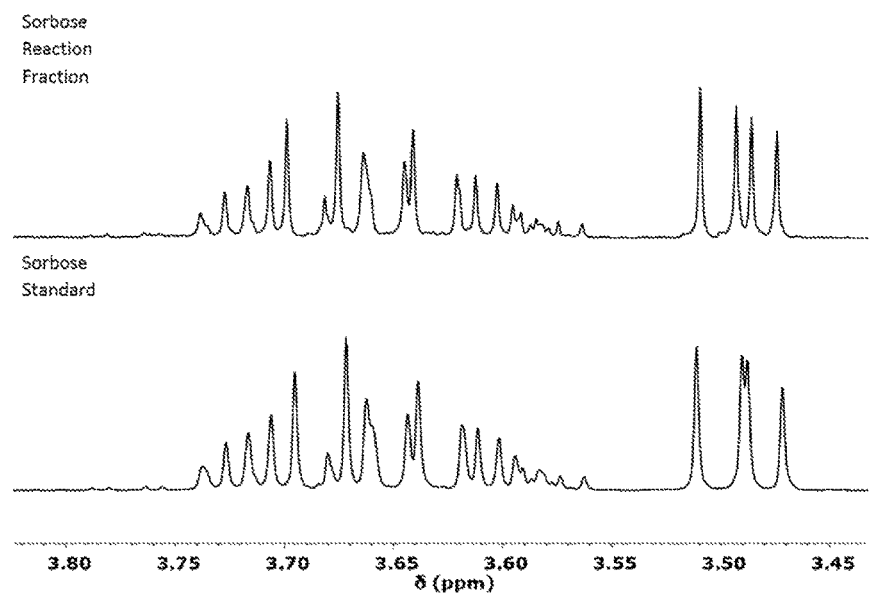
FIG. 9 shows $^1H$ NMR spectra of L-sorbose standard solution and of the sorbose-containing fraction isolated after reaction of D-fructose with $MoO_3$ in water at 100° C. for 4 h.
Figure 10:
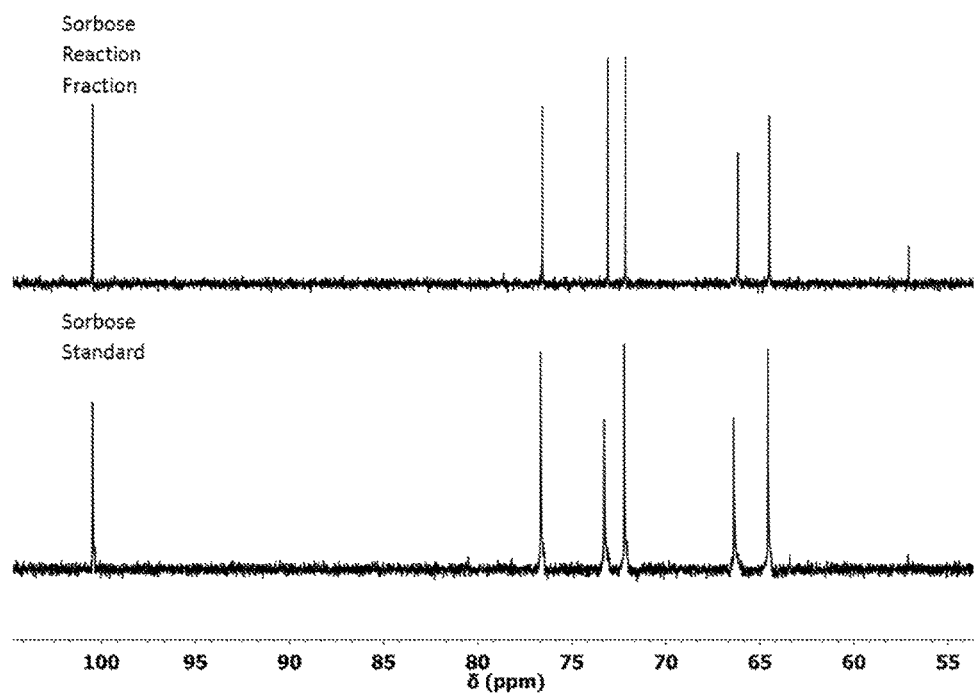
FIG. 10 shows $^{13}C$ NMR spectra of L-sorbose standard solution and of the sorbose-containing fraction isolated after reaction of D-fructose with $MoO_3$ in water at 100° C. for 4 h.
Figure 11:
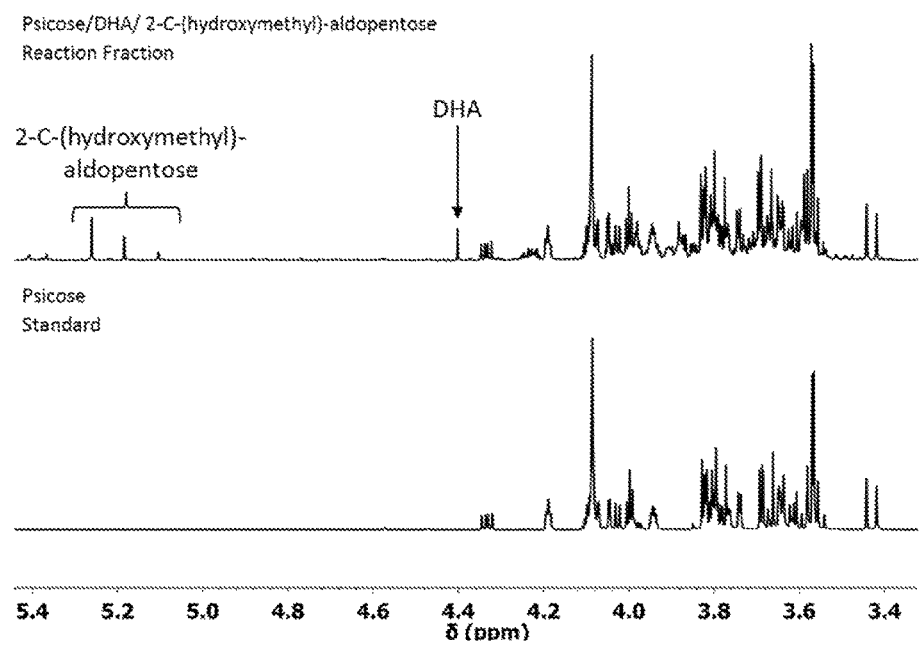
FIG. 11 shows $^1H$ NMR spectra of D-psicose standard solution and of the psicose-containing fraction isolated after reaction of D-fructose with $MoO_3$ in water at 100° C. for 4 h. DHA and a 2-C-(hydroxymethyl)-aldopentose are present in the collected fraction. HDO peak ca. 4.8 ppm is digitally suppressed for clarity.
Figure 12:
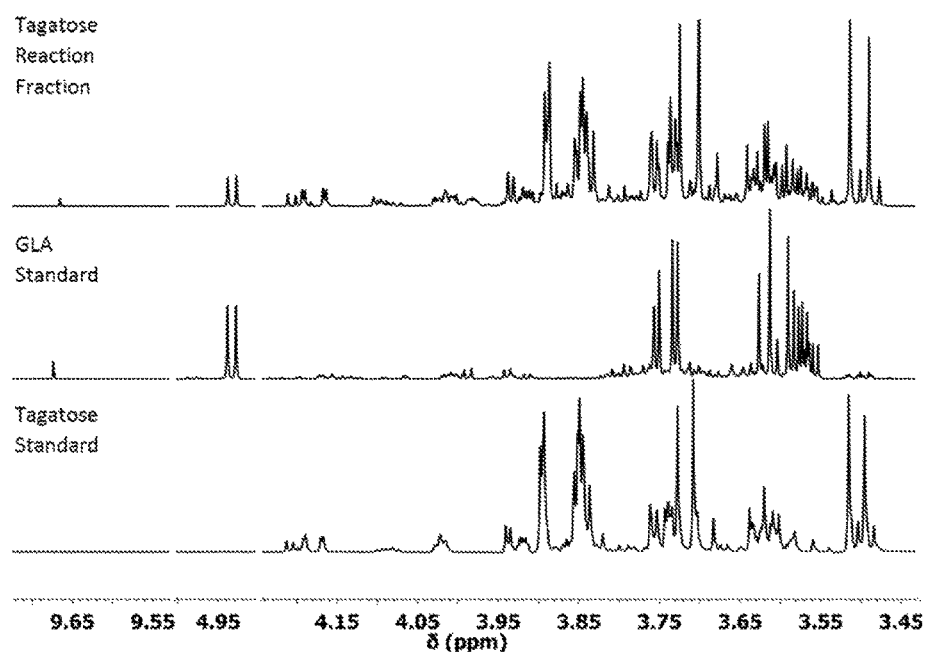
FIG. 12 shows $^1H$ NMR spectra of D-tagatose and GLA standard solutions and of the tagatose-containing fraction isolated after reaction of D-fructose with $MoO_3$ in water at 100° C. for 4 h. Glyceraldehyde is present in the collected fraction.
Figure 13:
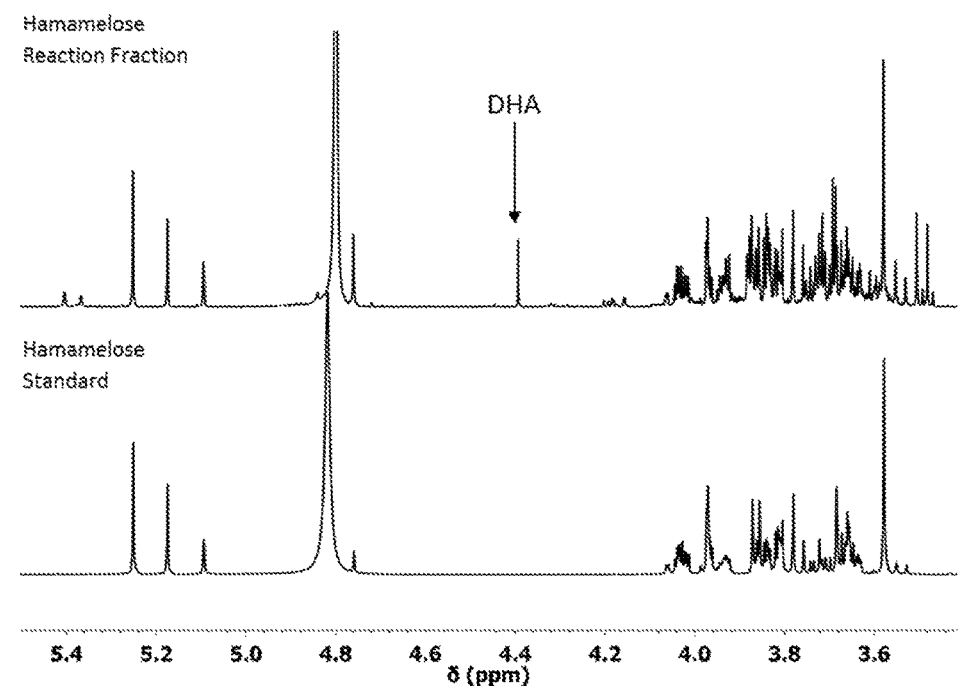
FIG. 13 shows $^1H$ NMR spectra of D-Hamamelose and of the hamamelose-containing fraction isolated after reaction of D-fructose with $MoO_3$ in water at 100° C. for 4 h. DHA and an unknown are present in the collected fraction.

While the low production of 2-C-(hydroxymethyl)-aldopentoses may be due to thermodynamic limitations (e.g. hamamelose-fructose equilibrium $K_{eq}$~14), tagatose and psicose may have formed in small quantities due to kinetic reasons. The sorbose, tagatose, and psicose tetradentate structural analogues of the fructose-molybdate complex that was previously hypothesized to be the key species in the fructose-hamamelose rearrangement are shown in FIG. 7 (along with analogs for other ketohexoses). $^1$H and $^{13}$C NMR studies of the molybdate complexes of ketohexoses suggested that only fructose and sorbose formed detectable amounts of tetradentate molybdate complexes, while psicose and tagatose tended to form tridentate complexes. These results suggested that aldol coupling reactions that would result in the formation of tagatose and psicose would proceed through a more energetic transition state, resulting in slow formation kinetics. Additionally, the same study provided estimates of the fraction of a given ketohexose that existed in a molybdate complex, indicating that the psicose and tagatose complexes were more favorable, with 80-95% of the sugars bound to Mo, whereas the value for sorbose and fructose was only 15-20%. If the retro-aldol reactions of ketohexoses proceeded through tetradentate molybdate complexes, these results suggested that the formation of tagatose and psicose, through the course of the reaction, may have reduced the fraction of catalytically active molybdate species through competitive binding and formation of tridentate complexes. A similar NMR study of molybdate and tungstate complexes of fructose and sorbose provided conflicting interpretations of complex structures. The multinuclear NMR data from this study suggested that both sugars form O-1,2,2',4 acyclic complexes, which do not involve O-3 coordination, in high proportions. It is important to note that these results were obtained at pH ca. 7.5, while, at lower pH, additional minor complexes were observed with proposed O-3,4,5,6 coordination. Molybdate-catalyzed epimerization of aldohexoses have been reported to be ~20-fold faster at pH 1.5-3.5 than at pH 5.9, and a lack of reaction was observed at pH higher than 6.0. Furthermore, 3-deoxy-aldohexoses do not undergo epimerization reactions, further supporting the requirement of binding through the hydroxyl group adjacent to the carbonyl. The combination of these results illustrated the complexity of molybdate-sugar equilibria, and implicated tetradentate complexes of fructose and sorbose in the retro-aldol reactions.

Although binuclear molybdate species were implicated in epimerization reactions catalyzed by water-dissolved $MoO_3$, higher structures containing molybdate ions were later shown to also catalyze epimerization reactions, e.g., Keggin structure molybdenum-based polyoxometalates, and heptamolybdate species immobilized on anion exchange supports. Similarly, the promotion of retro-aldol reactions of fructose were observed using the $H_3PMo_{12}O_{40}$ Keggin ion, and by $(NH_4)_6Mo_7O_{24}$, both as homogeneous catalysts and when immobilized onto an anion exchange support, e.g., Amberlite IRA-400, chloride form. Soluble and insoluble molybdate salts, e.g., $Na_2MoO_4$ and $ZnMoO_4$, respectively, as well as insoluble solids containing Mo(IV), e.g., $MoO_2$, and $MoS_2$, also are catalytically active in retro-aldol reactions of fructose in these studies. At this time, it is not clear whether the nominal form of each starting compound was the catalytically active one, or whether unknown catalytic species are generated in situ at reaction conditions. Due to the aforementioned complications in quantification, we could not directly assess the performance of each catalyst in retro-aldol reactions. However, we did observe differences in kinetics (see below) of the lactate-forming reaction cascade when different Mo-containing species were used for the retro-aldol component of the pathway, i.e., r3 of cascade consisting of r3, and r7-r9 in FIG. 4.

Tungstate analogs of molybdate-monosaccharide complexes have been reported to have formation constants that are 2-3 orders of magnitude higher than molybdates. Such strong binding may be responsible for the apparent lack of catalytic activity of $H_2WO_4$ and $H_3PW_{12}O_{40}$ in the epimerization of glucose to mannose at mild conditions. Similarly, in these experiments, tungstate species performed poorly but did produce species consistent with retro-aldol reactions of hexoses at long reaction times. Interestingly, at high temperatures (≥150° C.), $H_xWO_3$ was recently reported to catalyze retro-aldol reactions of glucose and fructose, when coupled with a Ru/C-promoted H2-reductive step to produce glycols. An apparent activation energy of 141.3 kJ/mol for the retro-aldol reaction of glucose was reported, whereas the apparent activation energy for further reactions of glycolaldehyde (including aldol condensation) was estimated to be 52.7 kJ/mol (23). These results illustrate the high barriers of retro-aldol reactions.

Nickel(II) diamine complexes in methanolic solutions were previously shown to catalyze the 1,2-CS in aldoses and 2-C-(hydroxymethyl)-aldopentose formation from ketohexoses at temperatures around 60° C. [Ni(N,N,N',N'-Me$_4$en)$_2$]Cl$_2$ in methanol was also seen to accelerate the retro-aldol part of the methyl lactate-producing reaction cascade at temperatures around 100° C.

Figure 14:
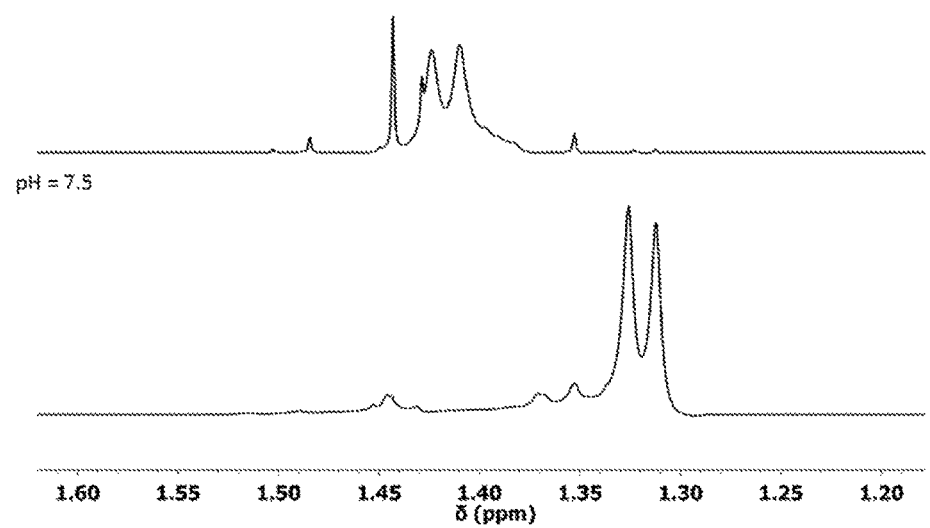
FIG. 14 shows $^1H$ NMR spectra of methyl group in molybdate-lactate complex formed in the reaction of D-fructose with $MoO_3$ and Sn-MFI in water at 100° C. for 16 h. Top spectrum (pH=2.5) is of a reaction aliquot prior to pH adjustment to 7.5 (bottom spectrum) by addition of sodium bicarbonate.
Figure 15:
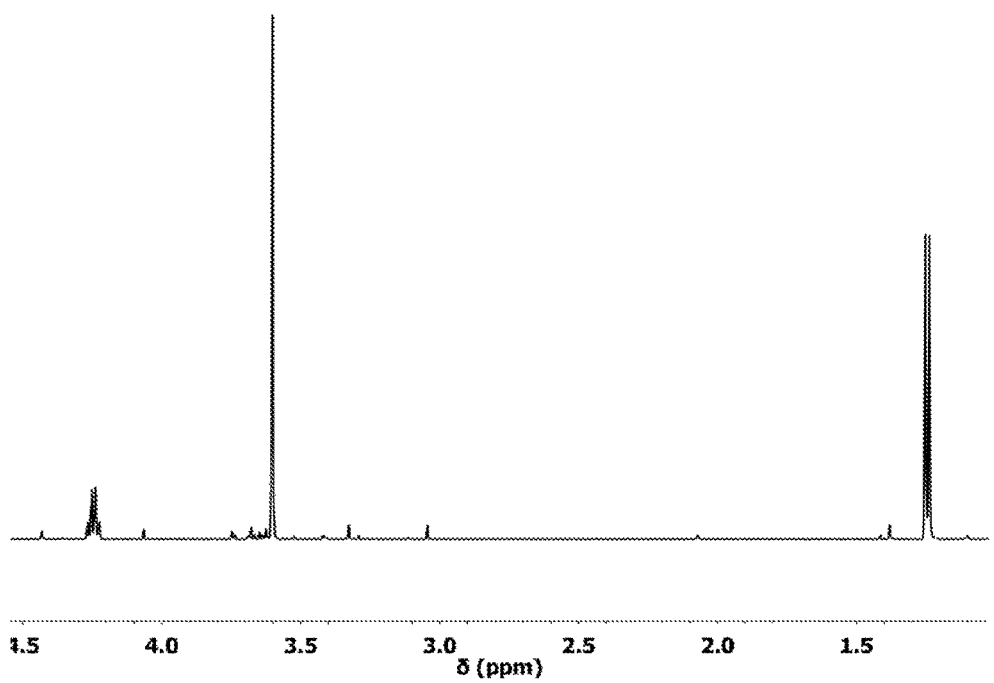
FIG. 15 shows $^1H$ NMR spectra of reaction solution of D-fructose with $MoO_3$ and Sn-MFI in MeOH at 100° C. for 30 h (ca. 68% methyl lactate yield) showing the three intense resonances of methyl lactate (ca. 1.25, 3.60, and 4.25 ppm) and small peaks associated with by-products. MeOH peak ca. 3.19 ppm is digitally suppressed for clarity.

Because materials that can catalyze the 1,2-intramolecular carbon shifts in aldoses were reported to be poor 1,2-intramolecular hydride shift catalysts for the same substrates, they did not enable a route to the more thermodynamically stable lactate products. As a result, retro-aldol intermediates, trioses, were observed. Addition of a 1,2-intramolecular hydride shift co-catalyst (Sn-MFI with Si/Sn=70±6, synthesized to be fluoride free) to a 1 wt % fructose, 0.2 wt % $MoO_3$ aqueous solution enabled rapid formation of lactate at 100° C. However, $^1$H NMR data suggested that at reaction conditions, lactate formed a strong complex with molybdate species, consistent with a previous study of pH-dependent molybdate-lactate interactions (Data in FIG. 14 show the shift in $^1$H NMR resonance of the methyl group of lactate when the pH of the reaction product was adjusted from 2.5 to 7.5 by addition of sodium bicarbonate). Quantitative $^1$H NMR indicated that lactate production stopped once stoichiometric amount of 2 mole lactate per mole molybdate was produced, suggesting inhibition of catalysis by product coordination.

Figure 17:
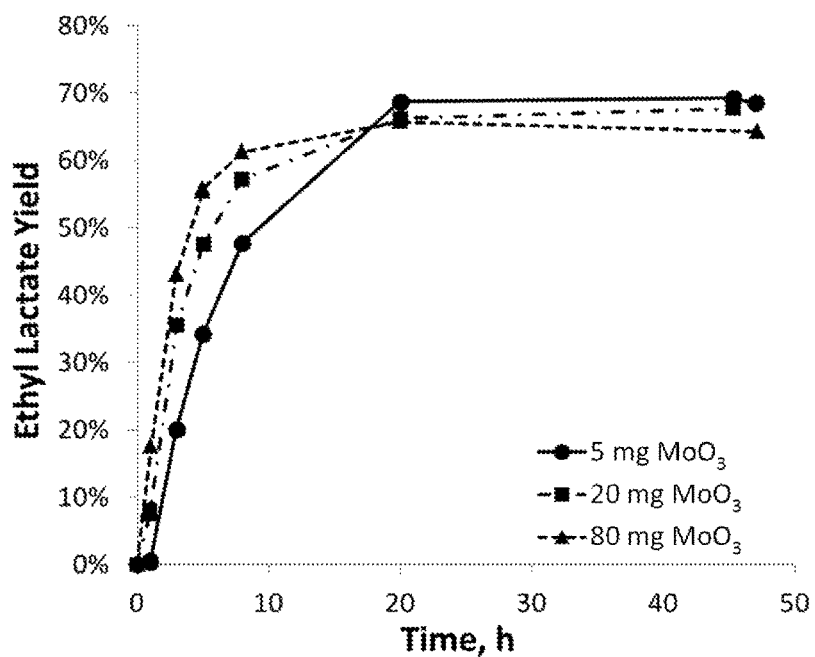
FIG. 17 provides data for ethyl lactate yield as a function of time for varying $MoO_3$ catalyst amounts (indicated in legend). Reaction conditions: 100° C.; 100 mg Sn-MFI; 50 mg D-fructose; 4.9 g EtOH; 50 mg naphthalene as internal standard.

When the reactions of fructose with $MoO_3$ and Sn-MFI were performed in alcoholic media, the bulk of $MoO_3$ did not dissolve and the corresponding alkyl lactates were produced in good yield (upwards of 75% at full fructose conversion). Turnover numbers (TONs) in excess of unity indicate that alkyl lactate production was truly catalytic in such reactions, e.g., for reaction 6 in Table 1, the TON≥5.5 based on Mo atoms for the retro-aldol reaction of fructose, and TON≥16.1 based on Sn atoms for lactate formation from the resulting trioses.

lactate yield, suggesting that side reactions may have comparable activation energies to the limiting steps in lactate production. Data in FIG. 17 (Table 1, reactions 2, 5, and 6) showed that, at 100° C., with constant Sn-MFI amount, increase of $MoO_3$ catalyst amount leads to a faster approach to ultimate lactate yield, but the increase in rate is not proportional to catalyst amount, and a potential induction

TABLE 1

Maximum observed yields of lactic acid or alkyl lactates obtained under various reaction conditions.

| Reaction | 1,2-CS catalyst | Mass, mg | 1,2-HS catalyst | Mass, mg | Substrate | Wt % | Yield, %@ |
|---|---|---|---|---|---|---|---|
| 1 [a] | $MoO_3$ | 80 | Sn-MFI | 100 | Fructose | 1 | 67.4 |
| 2 | $MoO_3$ | 80 | Sn-MFI | 100 | Fructose | 1 | 65.7 |
| 3 [b] | $MoO_3$ | 80 | Sn-MFI | 100 | Fructose | 1 | 61.9 |
| 4 [c] | $MoO_3$ | 80 | Sn-MFI | 100 | Fructose | 1 | 63.2 |
| 5 | $MoO_3$ | 20 | Sn-MFI | 100 | Fructose | 1 | 67.7 |
| 6 | $MoO_3$ | 5 | Sn-MFI | 100 | Fructose | 1 | 69.2 |
| 7 | $MoO_3$ | 80 | Sn-MFI | 200 | Fructose | 1 | 68.6 |
| 8 | $MoO_3$ | 80 | Sn-MFI | 50 | Fructose | 1 | 46.7 |
| 9 | $MoO_3$ | 80 | Sn-MFI | 100 | Fructose | 5 | 21. |
| 10 | $MoO_3$ | 80 | Sn-MFI | 100 | Fructose | 0.2 | 74.6 |
| 11 | none | 0 | Sn-MFI | 100 | Fructose | 1 | 3.9 |
| 12 | none | 0 | Sn-MFI | 100 | DHA/GLA | 0.5/0/5 | 86.5 |
| 13 | $MoO_3$ | 80 | none | 0 | Fructose | 1 | 13.0 |
| 14 | $MoO_3$ | 80 | none | 0 | DHA/GLA | 0.5/0/5 | 14.6 |
| 15 | $MoO_3$ | 80 | Sn-MFI | 100 | Fructose | 1 | 58.1 |
| 16 | $MoO_3$ | 80 | Sn-MFI | 100 | Fructose | 1 | 48.3 |
| 17 | $H_3PMo_{12}O_{40}$ | 10 | Sn-MFI | 100 | Fructose | 1 | 51.6 |
| 18 [d] | $Ni(Me_4en)_2Cl_2$ | 2 | Sn-MFI | 100 | Fructose | 1 | 14.6* |
| 19 [d] | $Ni(Me_4en)_2Cl_2$ | 20 | Sn-MFI | 100 | Fructose | 1 | 45.1* |
| 20 [d] | $TiO_2$—$SiO_2$ | 200 | Sn-MFI | 100 | Fructose | 1 | 7.7 |
| 21 | $MoO_3$ | 80 | Sn-Beta | 50 | Fructose | 1 | 51.0 |
| 22 | $MoO_3$ | 80 | Sn-Beta | 50 | Glucose | 1 | 40.2 |
| 23 | none | 0 | Sn-Beta | 50 | DHA | 1 | 88.4 |
| 24 | $MoO_3$ | 80 | Sn-MFI | 100 | Hamamelose | 1 | 70.2 |
| 25 | $MoO_3$ | 80 | Sn-MFI | 100 | Sorbose | 1 | 67.6 |
| 26 | $MoO_3$ | 80 | Sn-MFI | 100 | Psicose | 1 | 57.6 |
| 27 | $MoO_3$ | 80 | Sn-MFI | 100 | Tagatose | 1 | 46.1 |
| 28 [d] | $MoO_3$ | 80 | Sn-MFI | 100 | Fructose | 1 | 68.2 |
| 29 [e] | $MoO_3$ | 80 | Sn-MFI | 100 | Fructose | 1 | 22.7 |
| 30 [f] | $MoO_3$ | 10 | Sn-MFI | 100 | Fructose | 1 | 26.7† |

Reactions were performed in 10-mL thick-walled crimp-sealed glass reactors that were heated in a temperature-controlled oil bath. Aliquots (~100 μL) were extracted and filtered with a 0.2-μm polytetrafluoroethylene syringe filter before analysis. Reaction conditions: for each reaction, the catalyst amounts, substrate concentrations, solvents, and temperature used are indicated in the table. Each reaction involving alcoholic solvents was performed with 4.9 g of solvent and 50 mg of naphthalene as internal standard for GC-FID quantification. Unless otherwise indicated, reactions done in ethanol at 100° C.
@Maximum yield, carbon basis.
[a] Reaction at 90° C.;
[b] reaction at 110° C.;
[c] reaction at 120° C.;
[d] In methanol;
[e] In 90% ethanol/10% water;
[f] In water
*For reactions with $[Ni(N,N,N',N'-Me4en)_2]Cl_2$, aliquots were agitated with 20 mg of Dowex 50WX2 (hydrogen form) resin to remove nickel(II) species before filtration.
†For the reaction performed in water, no naphthalene was added, and 4,4-dimethyl-4-silapentane-1-sulfonic acid, sodium salt (DSS) was used as an external standard for quantitative $^1$H-NMR.

For reactions performed in alcoholic media, $MoO_3$ particles remained undissolved and progressively turned a dark-blue color, suggesting the possibility of partial reduction of the oxide or coverage with alcohol-insoluble molybdate-lactate complex. Both possibilities could contribute to lowering of lactate yield. Reversible ketalization of ketoses by the solvent was observed, and may be responsible for a retardation of alkyl lactate production.

Figure 16:
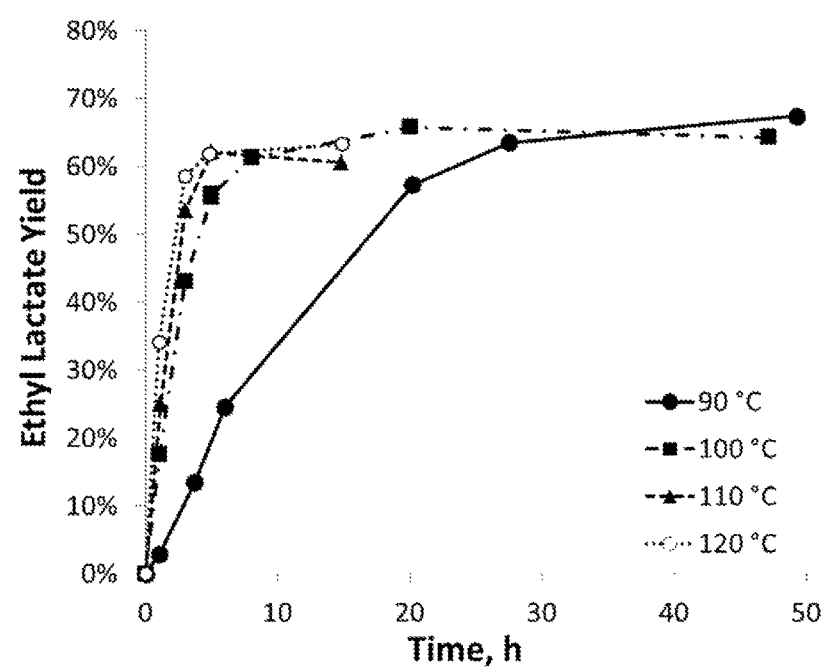
FIG. 16 provides data for ethyl lactate yield as a function of time at different temperatures (indicated in legend). Reaction conditions: 80 mg $MoO_3$; 100 mg Sn-MFI; 50 mg D-fructose; 4.9 g EtOH; 50 mg naphthalene as internal standard.
Figure 18:
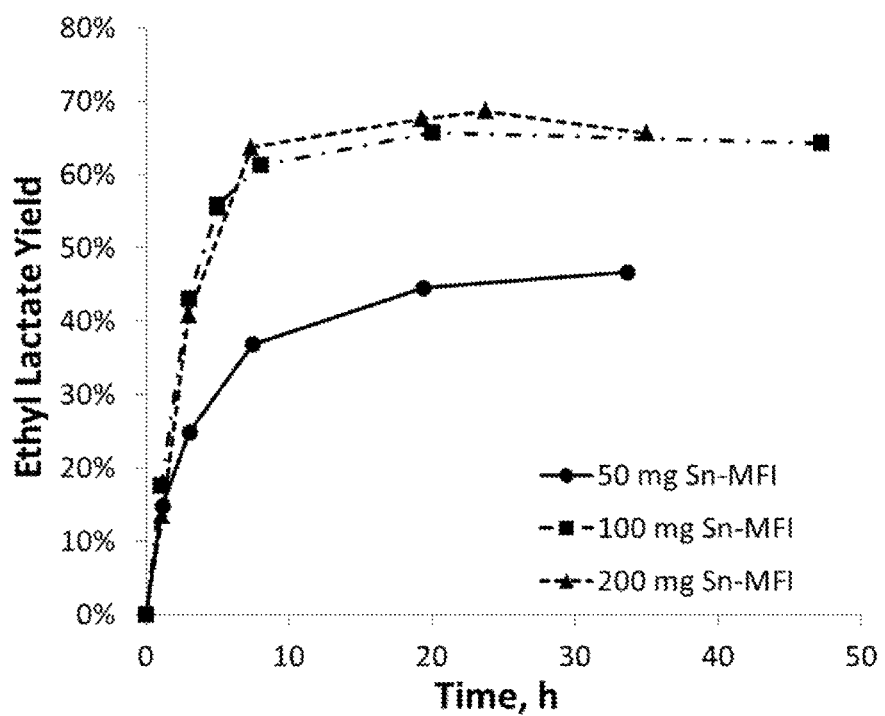
FIG. 18 provides data for ethyl lactate yield as a function of time for varying Sn-MFI catalyst amounts (indicated in legend). Reaction conditions: 100° C.; 80 mg $MoO_3$; 50 mg D-fructose; 4.9 g EtOH; 50 mg naphthalene as internal standard.
Figure 19:
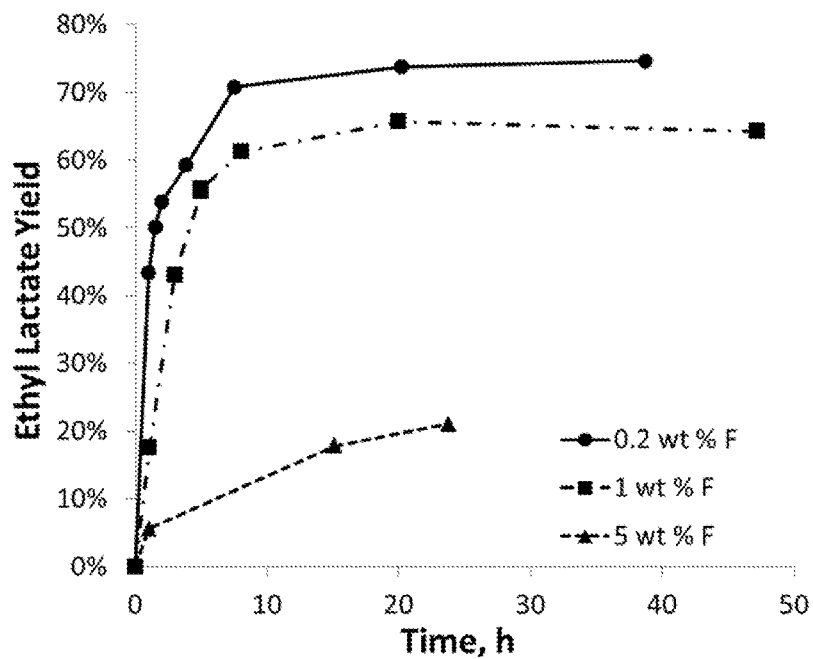
FIG. 19 provides data for ethyl lactate yield as a function of time for varying concentrations of fructose (indicated in legend). Reaction conditions: 100° C.; 80 mg $MoO_3$; 100 mg Sn-MFI; 4.9 g EtOH; 50 mg naphthalene as internal standard.

A number of parameters were varied in order to maximize the yield of lactate products and gain further insight into the limiting factors of this reaction network. Unless otherwise stated, the reactions were run in EtOH as solvent (see Table 1). Data in FIG. 16 (Table 1, reactions 1-4) showed that increase in temperature led to increase in rate of ethyl lactate formation, but did not significantly impact ultimate ethyl time was observed for the reaction with lowest $MoO_3$ content. Conversely, fixing the amount of $MoO_3$, and varying the amount of Sn-MFI suggested that two regimes were possible: one where the ethyl lactate production was limited by retro-aldol reactions, i.e., excess Sn-MFI catalyst had the potential to deplete trioses at a rate higher than their rate of generation by retro-aldol reactions, and the other where the ethyl lactate production from trioses was kinetically relevant, i.e., insufficient Sn-MFI led to accumulation of trioses (reactions 2, 7, and 8 in Table 1, and FIG. 18). In the former scenario, the ultimate yield of ethyl lactate was higher than in the latter. Similarly, at fixed amounts of both catalysts, lower initial substrate concentrations resulted in higher ethyl lactate yields (reactions 2, 9, and 10 in Table 1, and FIG. 19). These data suggest that high concentrations of substrate and intermediates are conducive to side-product formation and that rapid conversion to stable alkyl lactate products can reduce the extent of irreversible side reactions.

Figure 20:
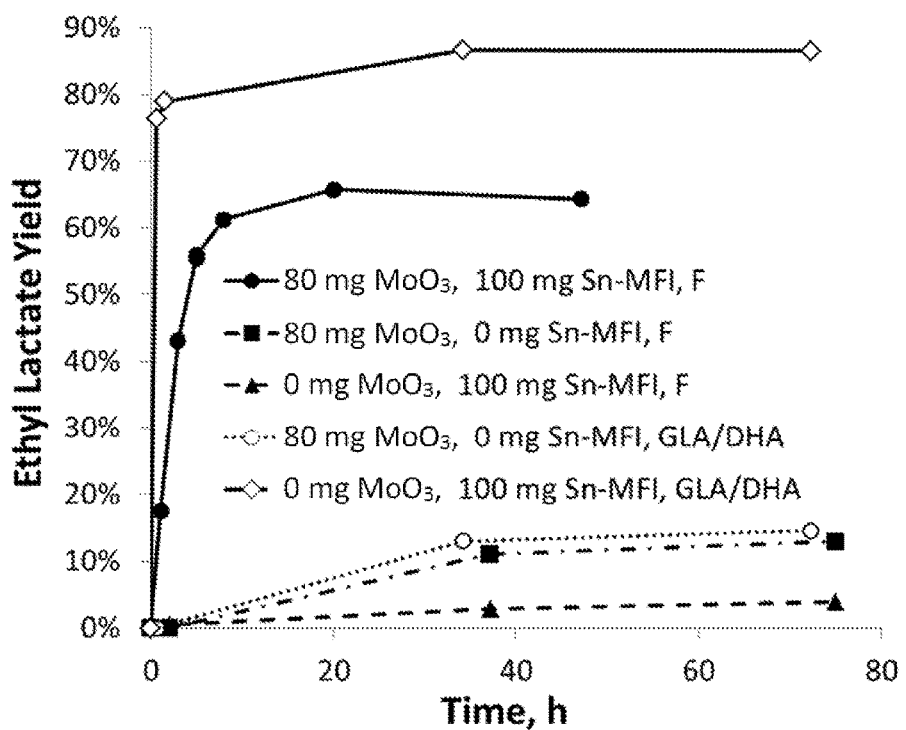
FIG. 20 provides data for ethyl lactate yield as a function of time for control runs illustrating the necessity of catalyst. Reaction conditions: 100° C.; catalyst amounts specified in legend; 50 mg of D-fructose (F) or mixture of 25 mg of GLA and 25 mg DHA (GLA/DHA) 4.9 g EtOH; 50 mg naphthalene as internal standard.
Figure 21:
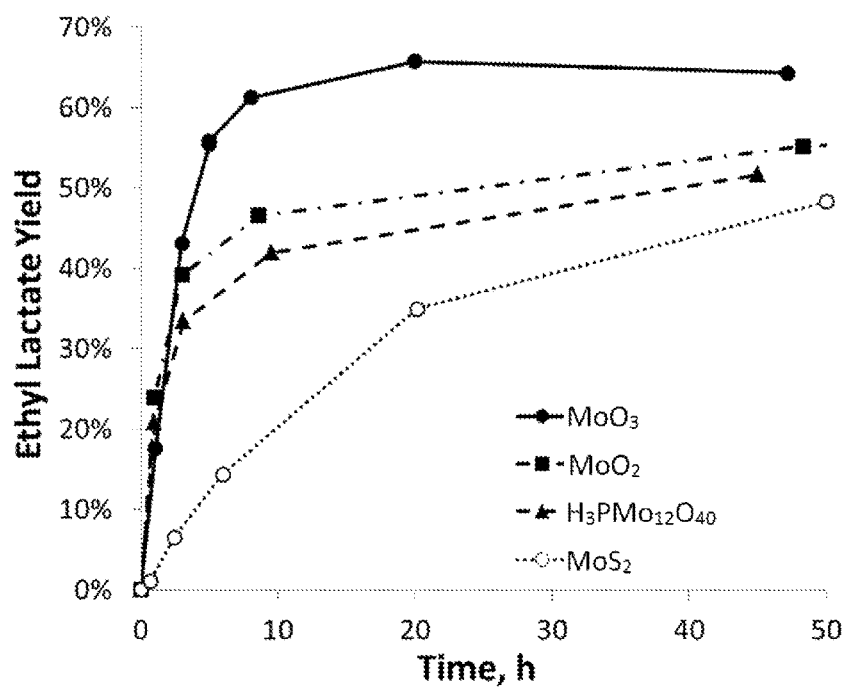
FIG. 21 provides data for ethyl lactate yield as a function of time for varying Mo-containing retro-aldol catalysts (indicated in legend). Reaction conditions: 100° C.; 100 mg Sn-MFI; 50 mg D-fructose; 4.9 g EtOH; 50 mg naphthalene as internal standard.

Results from control experiments that illustrate the importance of the combination of the two catalysts are shown in FIG. 20. In the absence of $MoO_3$ co-catalyst, Sn-MFI was unable to convert fructose to ethyl lactate in significant yields, even though high yields of ethyl lactate were rapidly achieved by Sn-MFI alone when an equimolar mixture of DHA and GLA were used as substrates. Conversely, without Sn-MFI, $MoO_3$ slowly catalyzed the formation of ethyl lactate from fructose, with an ultimate ethyl lactate yield being considerably lower than in the mixed-catalyst system. Additionally, the use of equimolar DHA and GLA mixture as starting substrate did not result in significantly higher yields of ethyl lactate when $MoO_3$ was used by itself, further illustrating the rapidity of side reactions of trioses. The $MoO_3$ and Sn-MFI combination was not the only one capable of catalyzing the conversion of fructose to lactates. FIG. 21 show that other Mo-containing catalysts such as $MoO_2$, $H_3PMo_{12}O_{40}$, and $MoS_2$ were also able to accelerate the retro-aldol part of the reaction cascade. Additionally, salts of molybdate (e.g. $Na_2MoO_4$ and $(NH_4)_6Mo_7O_{24}.4H_2O$) also catalyzed the retro-aldol reaction of fructose, both as homogeneous catalysts and when immobilized onto an anion-exchange support (e.g. Amberlite IRA-400, chloride form). While the conditions for these catalysts have not been optimized, all alternative Mo-containing catalysts resulted in lower ethyl lactate yields than were achieved with $MoO_3$.

Figure 22:
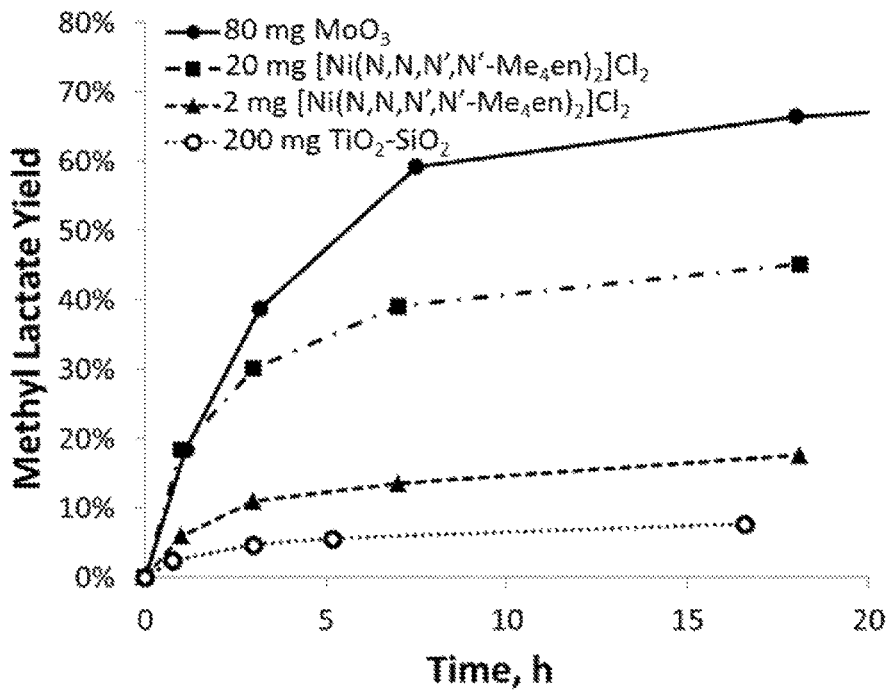
FIG. 22 provides data for methyl lactate yield as a function of time for $MoO_3$ and [Ni(N,N,N',N'-$Me_4$en)$_2$]$Cl_2$ catalysts (amounts indicated in legend). Reaction conditions: 100° C.; 100 mg Sn-MFI; 50 mg D-fructose; 4.9 g MeOH; 50 mg naphthalene as internal standard.

Nickel (II) diamine complexes in methanolic solutions were previously shown to catalyze the 1,2-intramolecular carbon shifts in aldoses and 2-C-(hydroxymethyl)-aldopentose formation from ketohexoses ca. 60° C. Data in FIG. 22 show that the tetramethylethylenediamine complex with $NiCl_2.6H_2O$ ([$Ni(N,N,N',N'-Me_4en)_2$]$Cl_2$) in methanol also accelerated the retro-aldol part of the reaction cascade ca. 100° C. The investigators of 1,2-intramolecular carbon shift catalysis in aldoses by nickel (II) diamine complexes used stoichiometric amounts of nickel complexes and aldoses, noting that the nickel complexes can also be used in catalytic amounts, but deactivate after a few turnovers. Similarly, deactivation could be responsible for the early decrease in the methyl lactate production rate apparent in the data in FIG. 22.

Figure 23:
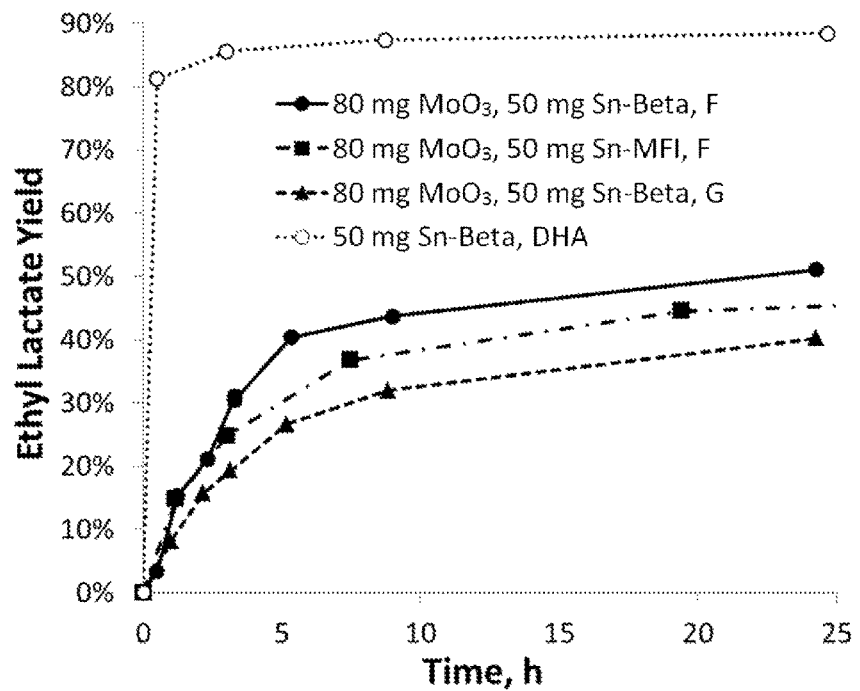
FIG. 23 provides data for ethyl lactate yield as a function of time for Sn-Beta/Sn-MFI comparison. Reaction conditions: 100° C.; 80 mg $MoO_3$; Sn-Beta or Sn-MFI amount specified in legend; 50 mg of D-fructose (F), D-Glucose (G), or DHA; 4.9 g EtOH; 50 mg naphthalene as internal standard.

Data in FIG. 23 (Table 1, reactions 21-23) show that Sn-Beta (Si/Sn=95±14, synthesized using fluoride sources) can be used in place of Sn-MFI for the second part of the reaction cascade. Furthermore, under conditions where the lactate formation from trioses was kinetically relevant, Sn-Beta performed better than Sn-MFI. This result was consistent with the reported faster kinetics of alkyl lactate synthesis from trioses by Sn-Beta than Sn-MFI. Because Sn-Beta can also catalyze glucose-fructose-mannose isomerization reactions and, to some degree, retro-aldol reactions of hexoses, Sn-Beta was not used as the catalyst of choice in the current study, in order to avoid additional complicating factors in the reaction network. To illustrate this point, data in FIG. 23 show the production of ethyl lactate from glucose when Sn-Beta is used in combination with $MoO_3$, indicating that aldose-ketose isomerization reactions occur on kinetically relevant timescales. Another noted benefit of using Sn-MFI as the 1,2-HS catalyst is that it can be easily synthesized in the absence of fluoride (a frequently raised concern for large-scale syntheses of catalysts to be used for biomass processing, e.g., Sn-Beta). In principle, even more economically accessible materials that can catalyze lactate formation from trioses, e.g., post-synthetically treated Al zeolites or homogeneous Lewis acids, may be paired with the retro-aldol catalysts reported in this study to produce alkyl lactates from hexoses at mild conditions.

Sn-Beta (and other Lewis acid-containing zeotypes, e.g., Ti-Beta) has also been shown to catalyze the 1,2-CS reactions of aldoses in aqueous solutions when either borate or alkali salts are present. The recently reported increase in methyl lactate production by Sn-Beta from fructose in methanol at 170° C. (from 16% to 57%) upon alkali carbonate addition is consistent with formation of 1,2-CS sites upon alkali exchange of open sites in Sn-Beta. Sn-Beta systems with added borate and alkali salts were reported to be pH sensitive and are not efficient 1,2-CS catalysts in acidic conditions. Furthermore, if Sn-MFI is used as a size-dependent 1,2-HS catalyst in conjunction with borate- or alkali-modified Sn-Beta, borate or alkali ions have the capacity to enter the Sn-MFI pores and influence the efficiency of lactate production from trioses. Thus, coupling of lactic acid or alkyl lactate production with retro-aldol reactions in mixed Sn-based zeotype systems may also be useful in affecting the distribution of $C_2$, $C_3$, and $C_4$ products by limitation of aldose-ketose interconversion.

Figure 24:
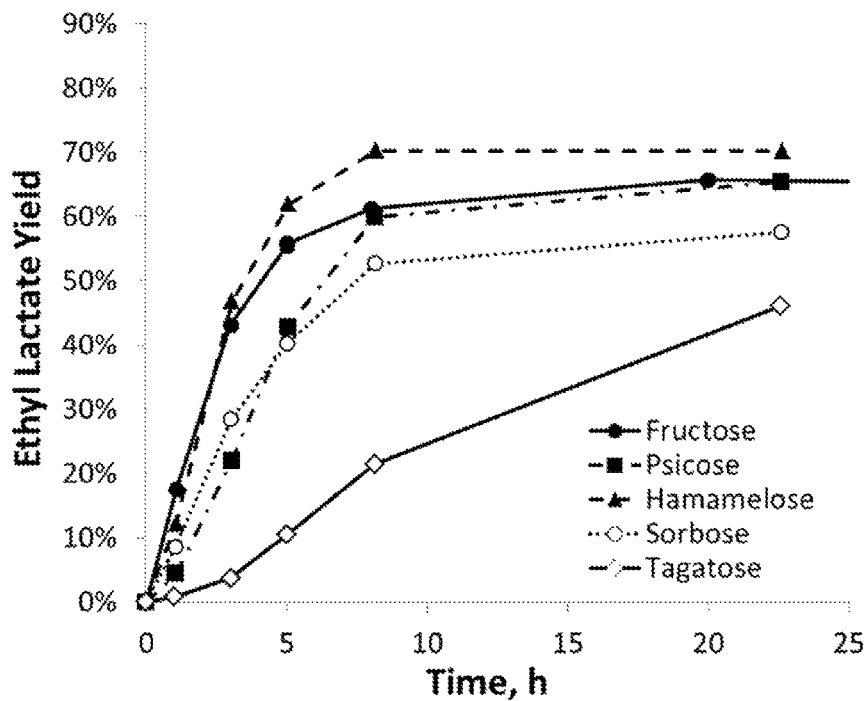
FIG. 24 provides data for ethyl lactate yield as a function of time for different ketohexoses and a 2-C-(hydroxymethyl)-aldopentoses (hamamelose) as substrates. Reaction conditions: 100° C.; 80 mg $MoO_3$; 100 mg Sn-MFI; 50 mg of D-fructose, D-psicose, D-hamamelose, L-sorbose, or D-tagatose; 4.9 g EtOH; 50 mg naphthalene as internal standard.

As noted earlier, formation of other 2-ketohexoses and 2-C-(hydroxymethyl)-aldopentoses is known to occur in $MoO_3$-catalyzed reactions of fructose. The differences in interactions between the various molybdate and hexose species may impact the rate of retro-aldol reactions. To test for this possibility, psicose, sorbose, tagatose, and hamamelose were reacted under the same conditions as fructose. Data in FIG. 24 (and Table 1, reactions 2 and 24-27) show that the initial rate of ethyl lactate formation from hamamelose was nearly identical to that from fructose. The initial rates of ethyl lactate formation from sorbose and psicose were lower than from fructose, but comparable ultimate yields of ethyl lactate were observed. Tagatose appeared to be the slowest to react. These results indicate that the formation of ketohexose side-products can impact the ultimate kinetics of ethyl lactate production.

Figure 25:
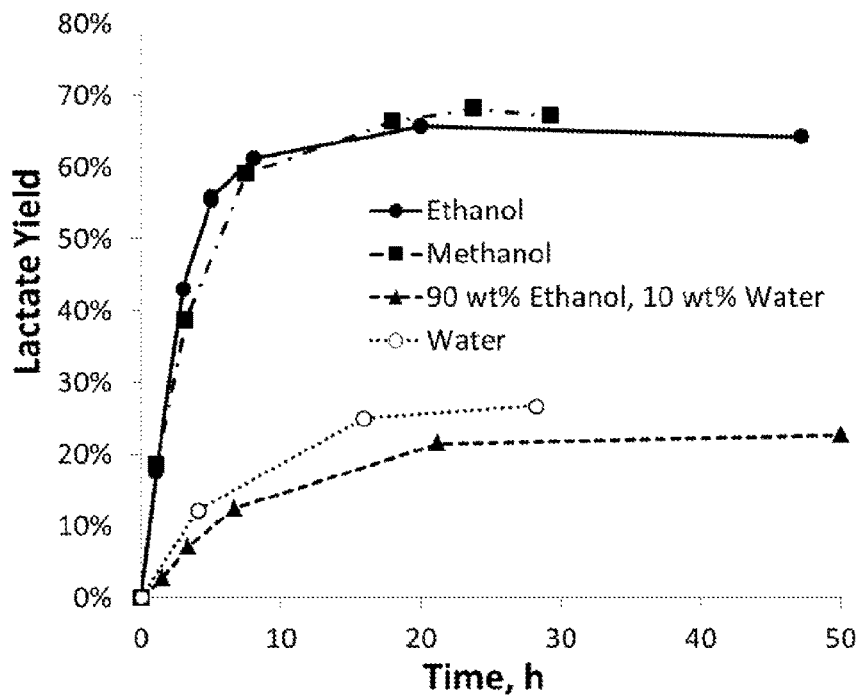
FIG. 25 provides data for alkyl lactate yield as a function of time for different solvents (specified in legend): 100° C.; 80 mg $MoO_3$; 100 mg Sn-MFI, 50 mg of D-fructose (F); 4.9 g solvent; 50 mg naphthalene as internal standard. In case of water, external standard (DSS) was used for $^1H$ NMR quantification instead of naphthalene.

At 160° C., Sn-Beta was reported to perform much better for lactate production from sucrose in methanol than in ethanol, isopropanol, or water. Here, for the case of $MoO_3$/Sn-MFI, no significant differences in kinetics or ultimate yields of alkyl lactates were observed between methanol and ethanol solvents, at 100° C. (reactions 2 and 28 in Table 1, and FIG. 24). However, when 10% (w/w) water/ethanol was used as a solvent, the ultimate yield of ethyl lactate was significantly lower than for neat ethanol (FIG. 25). This difference may be attributed to increased solubility of molybdate species in the mixed solvent system. Since lactic acid forms strong complexes with molybdate ions, this fraction of lactate species is missing from the yield.

In addition to the main alkyl lactate products quantified in this study, species consistent with retro-aldol reactions on aldohexoses and partially oxidized products were identified in the GC-MS chromatograms (e.g. ethyl acetals and ethyl esters of glycolaldehyde, glycolic acid, pyruvic acid, 2-hydroxy-3-butenoic acid, and 2,4-dihydroxybutanoic acid were observed for reactions in ethanol). Catalyst combinations that did not rapidly convert ketoses into alkyl lactates and generated Brønsted acidity also resulted in minor formation of 5-HMF and its partially oxidized variants, e.g., aqueous reactions of $H_3PMo_{12}O_{40}$ and Sn-MFI or $H_2MoO_4$ and Sn-MFI, after complete inhibitive complexation of lactic acid with molybdate. The aldohexoses that are required for C2 and C4 products are possibly formed in small amounts from ketohexoses by Sn sites on the external surface of Sn-MFI crystallites. The partially oxidized products may be formed by the reduction of Mo(VI) to Mo(V) and/or Mo(IV), since particles of $MoO_3$ appear to progressively turn dark blue over the course of the reaction.

Figure 26:
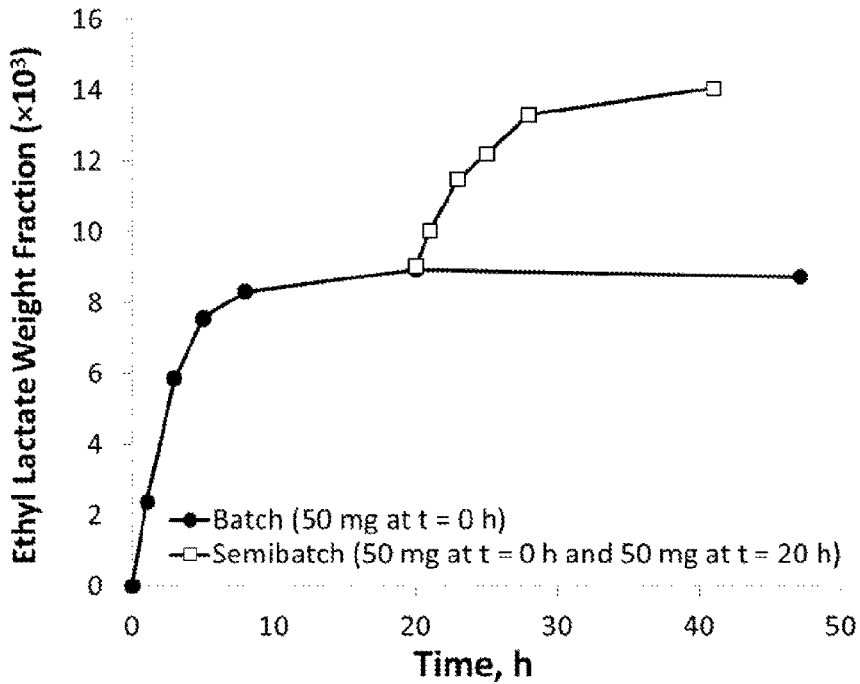
FIG. 26 provides data for ethyl lactate weight fraction as a function of time for batch and semi-batch reactions. Reaction conditions: 100° C.; 80 mg $MoO_3$; 100 mg Sn-MFI; 4.9 g EtOH; 50 mg naphthalene as internal standard. For batch operation, 50 mg of D-fructose was added at t=0 h. For semi-batch operation, 50 mg of D-fructose was added at t=0 h. After 20 h of reaction, the reactor was rapidly quenched with ice and opened. At this point, the first aliquot was taken and another 50 mg of D-fructose was added to the reactor. After re-sealing the reactor, regular operation and sampling procedure was resumed.

The use of moderate temperatures (~100° C.) enabled numerous desirable features for the production of lactic acid and alkyl lactate from hexoses such as lower process pressure and reduced catalyst deactivation due to product deposition on the catalysts. The minimal operating pressure for such reactions was autogenous, and was largely determined by the vapor pressure ($P_{sat}$) of the solvent. For instance, for methanol, $P_{sat}$=3.5 bar at 100° C. and Psat=21.9 bar at 170° C. Notably, in the case of reactions in ethanol at 100° C., after ethyl lactate production from the initially added fructose stopped, e.g., see data in FIG. 26, ~20 h, the $MoO_3$/Sn-MFI catalyst combination was still active without regeneration by calcination or washing, as indicated by further production of ethyl lactate upon introduction of additional fructose to the reaction solution. This was contrary to the coked state of Sn-Beta catalysts that required catalyst calcination after high-temperature reactions.

As those skilled in the art will appreciate, numerous modifications and variations of the present invention are possible in light of these teachings, and all such are contemplated hereby. All references cited within this disclosure are incorporated by reference herein, at least for their teachings in the context presented.

The following reference may be helpful in understanding certain aspects of the present disclosure.

(1) Werpy, T.; Petersen, G. Top Value Added Chemicals from Biomass: Volume I—Results of Screening for Potential Candidates from Sugars and Synthesis Gas; Golden, Colo., 2004; Vol. 1.
(2) Dusselier, M.; Van Wouwe, P.; Dewaele, A.; Makshina, E.; Sels, B. F. *Energy Environ. Sci.* 2013, 6 (5), 1415.
(3) Holm, M. S.; Saravanamurugan, S.; Taarning, E. *Science* 2010, 328 (5978), 602.
(4) Dusselier, M.; Van Wouwe, P.; de Clippel, F.; Dijkmans, J.; Gammon, D. W.; Sels, B. F. *Chem Cat Chem* 2013, 5 (2), 569.
(5) Huber, G. W.; Iborra, S.; Corma, A. *Chem. Rev.* 2006, 106 (9), 4044.
(6) Dapsens, P. Y.; Mondelli, C.; Kusema, B. T.; Verel, R.; Perez-Ramirez, J. *Green Chem.* 2014, 16 (3), 1176.
(7) Taarning, E.; Saravanamurugan, S.; Spangsberg Holm, M.; Xiong, J.; West, R. M.; Christensen, C. H. *Chem Sus Chem* 2009, 2 (7), 625.
(8) Osmundsen, C. M.; Holm, M. S.; Dahl, S.; Taarning, E. *Proc. Royal. Soc. A* 2012, 468 (2143), 2000.
(9) Tolborg, S.; Sádaba, I.; Osmundsen, C. M.; Fristrup, P.; Holm, M. S.; Taarning, E. *Chem Sus Chem* 2015, 8 (4), 613.
(10) Wang, Y.; Deng, W.; Wang, B.; Zhang, Q.; Wan, X.; Tang, Z.; Wang, Y.; Zhu, C.; Cao, Z.; Wang, G.; Wan, H. *Nat. Commun.* 2013, 4 (Ii), 2141.
(11) Bermejo-Deval, R.; Orazov, M.; Gounder, R.; Hwang, S.-J.; Davis, M. E. *ACS Catal.* 2014, 4 (7), 2288.
(12) Bilik, V.; Petrus, L.; Farkas, V. *Chem. Zvesti* 1975, 29 (5), 690.
(13) Tanase, T.; Shimizu, F.; Kuse, M.; Yano, S.; Hidai, M.; Yoshikawa, S. *Inorg. Chem.* 1988, 27 (23), 4085.
(14) Hricovíniová, Z.; Hricoviní, M.; Petrus, L. *Chem. Pap.* 1998, 52 (5), 692.
(15) Hricovíniová, Z.; Lamba, D.; Hricoviní, M. *Carbohydr. Res.* 2005, 340 (3), 455.
(16) Yanagihara, R.; Osanai, S.; Yoshikawa, S. *Chem. Lett.* 1992, No. 1, 89.
(17) Stanković, E.; Bilik, V.; Fedoroňko, M.; Königstein, J. *Chem. Zvesti* 1975, 29 (5), 685.
(18) Petruš, L.; Petrušová, M.; Hricovíniová, Z. 2001; pp 15-41.
(19) Matulova, M.; Bilik, V. 1990, 44 (1), 97.
(20) Sauvage, J.-P.; Verchère, J.-F.; Chapelle, S. *Carbohydr. Res.* 1996, 286 (6), 67.
(21) Hayes, M. L.; Pennings, N. J.; Serianni, A. S.; Barker, R. *J. Am. Chem. Soc.* 1982, 104 (24), 6764.
(22) Caldeira, M. M.; Gil, V. M. S. *Polyhedron* 1986, 5 (1-2), 381.

What is claimed:

1. A method comprising contacting a carbohydrate feedstock with a tandem catalyst system at a temperature in a range of from 60° C. to 200° C., the contacting resulting in the formation of an α-hydroxy carboxylic acid or α-hydroxy carboxylic acid ester, wherein the carbohydrate feedstock comprises a monosaccharide; and
wherein the tandem catalyst system comprises two materially different discrete catalysts, the catalysts being:
(a) a first retro-aldol catalyst, wherein the first retro-aldol catalyst comprises
(i) an optionally substituted oxo(hydroxy)molybdate, an optionally substituted sulfomolybdate, an optionally substituted oxy(hydroxy)tungstate;
(ii) a Ni(II) diamine complex;
(iii) an alkali-exchanged hafno-, stanno-, titano-, or zirconosilicate, an optionally substituted amorphous hafnium-, tin-, titanium-, or zirconium-silicate co-precipitate; or
(iv) a combination thereof; and
(b) a second Lewis acid catalyst, wherein the Lewis acid catalyst comprises a crystalline microporous hafno-, stanno-, titano-, or zirconosilicate containing pores equal to or greater than 10-MR.

2. The method of claim 1, wherein the carbohydrate feedstock comprises a pentose or hexose monosaccharide, and the contacting results in the conversion of the pentose or hexose monosaccharide to the corresponding α-hydroxy carboxylic acid or α-hydroxy carboxylic acid ester.

3. The method of claim 1, wherein carbohydrate feedstock comprises an aldose or ketose monosaccharide, and the contacting results in the conversion of the aldose or ketose monosaccharide to the corresponding α-hydroxy carboxylic acid or α-hydroxy carboxylic acid ester.

4. The method of claim 1, wherein carbohydrate feedstock comprises glucose, mannose, fructose, psicose, sorbose, tagatose, or a combination thereof, and the contacting results in the conversion of the glucose, mannose, fructose, psicose, sorbose, tagatose, or a combination thereof, to the corresponding α-hydroxy carboxylic acid or α-hydroxy carboxylic acid ester.

5. The method of claim 1, wherein the first retro-aldol catalyst is capable of converting a pentose or hexose monosaccharide to a diose, triose, or tetrose intermediate.

6. The method of claim 1, wherein the first retro-aldol catalyst is derived from an oxomolybdate or sulfomolybdate precursor of $MoO_3$, $MoO_2$, $MoS_2$, $MoS_3$, $Mo_2S_5$, $MoO(OH)_2$, $MoO_4^{2-}$, $Mo_5O_{14}$, $Mo_2O_7^{2-}$, $Mo_{17}O_{47}$, $H_3PMo_{12}O_{40}$, $[Mo_7O_{24}]^{6-}$, or a combination thereof.

7. The method of claim 1, wherein the first retro-aldol catalyst comprises an ethylenediamine complex of Ni(II).

8. The method of claim 1, wherein the second Lewis acid catalyst is capable of converting a diose, triose, or tetrose intermediate to an α-hydroxy carboxylic acid or α-hydroxy carboxylic acid ester.

9. The method of claim 1, wherein the second Lewis acid catalyst comprises a tin-substituted silicate of beta or MFI topology.

10. The method of claim 1, where in the tandem catalyst system comprises a composite catalyst, comprising both the first retro-aldol catalyst and the second Lewis acid catalyst.

11. The method of claim 1, wherein the tandem catalyst system comprises polar aprotic solvent.

12. The method of claim 1, wherein the tandem catalyst system comprises an aqueous solvent.

13. The method of claim 1, wherein the tandem catalyst system comprises a solvent comprising at least one $C_{1-6}$ alcohol.

14. The method of claim 13, wherein the alcoholic solvent is substantially anhydrous.

15. The method of claim 1, wherein
  (a) the carbohydrate feedstock comprises a C5 or C6 aldose or ketose monosaccharide;
  (b) the first retro-aldol catalyst comprises an oxo(hydroxy)molybdate; and
  (c) the second Lewis acid catalyst comprises a Sn-beta or Sn-MFI zeolite; and
  (d) the tandem catalyst system further comprises an alcoholic solvent;
  wherein the contacting is done at a temperature in a range of from 60° C. to 140° C., so as to produce an α-hydroxy carboxylic acid or α-hydroxy carboxylic acid ester.

* * * * *